(12) United States Patent  (10) Patent No.: US 8,716,456 B2
O'Hare et al.  (45) Date of Patent: May 6, 2014

(54) PENTALENES

(75) Inventors: Dermot Michael O'Hare, Oxford (GB); Andrew Edward Ashley, Oxford (GB)

(73) Assignee: Isis Innovation Limited, Oxford (GB)

( * ) Notice: Subject to any disclaimer, the term of this patent is extended or adjusted under 35 U.S.C. 154(b) by 737 days.

(21) Appl. No.: 12/530,451

(22) PCT Filed: Mar. 10, 2008

(86) PCT No.: PCT/GB2008/000818
§ 371 (c)(1),
(2), (4) Date: Oct. 9, 2009

(87) PCT Pub. No.: WO2008/110774
PCT Pub. Date: Sep. 18, 2008

(65) Prior Publication Data
US 2010/0105883 A1  Apr. 29, 2010

(30) Foreign Application Priority Data
Mar. 9, 2007 (GB) .................................. 0704569.3

(51) Int. Cl.
*C07F 5/00* (2006.01)
*C07F 7/00* (2006.01)
*C07F 13/00* (2006.01)
*C07F 15/00* (2006.01)
*C07C 35/00* (2006.01)
*C07C 13/615* (2006.01)

(52) U.S. Cl.
USPC ................. 534/15; 534/11; 556/45; 556/108; 556/136; 556/150; 568/819; 585/21

(58) Field of Classification Search
USPC ........... 585/21; 534/11, 15; 556/45, 136, 150, 556/108; 568/819
See application file for complete search history.

(56) References Cited

U.S. PATENT DOCUMENTS 3,134,799 A   5/1964 Loev et al.
5,959,132 A   9/1999 Jonas et al.

FOREIGN PATENT DOCUMENTS

EP    0749985 A   12/1996
EP    0837068 A   4/1998
EP    0897926 A   2/1999
WO    99/07716    2/1999

OTHER PUBLICATIONS

Hartke et al., Chemische Berichte, 105(8):2584-2593 (1972).
Jones et al., Organometallics, 25:221-229 (2006).
Cloke, Geoffrey, Pure & Applied Chemistry, 73:223-238 (2001).
Cloke et al., Organometallics, 19:5795-5798 (2000).
Cloke et al., Organometallics, 18:1080-1086 (1999).
Ashley et al., Chemical Communications, 15:1512-1514 (2007).
Kusade, Kousouke, Bulletin of the Chemical Society of Japan, 56(2):481-486 (1983.
Hart et al., J. Am. Chem. Soc., 96(20):6436-6450 (1974).
International Search Report mailed Jan. 13, 2009 in PCT/GB2008/000818 (2 pages).
UKIPO Search Report dated Jul. 6, 2007 in GB0704569.3 (2 pages).

*Primary Examiner* — Porfirio Nazario Gonzalez
(74) *Attorney, Agent, or Firm* — Sam K. Tahmassebi; TechLaw LLP

(57) ABSTRACT

The present invention relates to per-substituted pentalene compounds, including permethylpentalene and precursors thereof. In particular, the invention provides substituted pentalene compounds and methods of preparing substituted pentalene compounds; complexes of metals with substituted pentalene compounds and methods for their production; and the use of complexes of metals with substituted pentalene compounds in catalysis.

25 Claims, No Drawings

PENTALENES

RELATED APPLICATIONS

This application is filed under 35 U.S.C. §371 as the U.S. national phase of International Application PCT/GB2008/000818, filed Mar. 10, 2008, which designated the U.S. and claims priority to GB Application No. 0704569.3, filed Mar. 9, 2007. The entire disclosure of both applications, including any drawings, is hereby incorporated herein by reference.

The present invention relates to substituted pentalene compounds. In particular, the invention provides substituted pentalene compounds and methods of preparing substituted pentalene compounds; complexes of metals with substituted pentalene compounds and methods for their production; and the use of complexes of metals with substituted pentalene compounds in catalysis.

Pentalene ($C_8H_6$, Pn) was first isolated, along with the 1,3 dimethyl substituted compound, from its parent dimer in the 1970s (K. Hafner, R. Doenges, E. Goedecke and R. Kaiser, *Angew. Chem.*, 1973, 85, 362-364). The latter was synthesised using the Hoffmann elimination of 1,2-dihydro-1-piperidino-dihydropentalene to furnish Pn transiently, which under the reaction conditions immediately forms its cyclobutane ring-fused adduct. Photolysis of this material at 254 nm and −196° C. gave Pn.

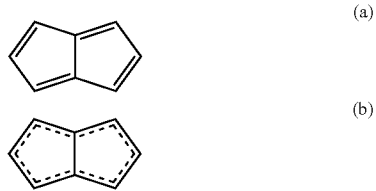

(a) $C_{2h}$ and (b) $D_{2h}$ structures of the pentalene molecule

More recent work has been able to produce clean samples of Pn within an Ar/$N_2$ matrix at the same temperature and has enabled the first detailed electronic and IR spectrum to be obtained (T. Bally, Z. Zhu, M. Neuenschwander and S. Chai, *J. Am. Chem. Soc.*, 1997, 119, 1869-1875).

Some substituted pentalene compounds have previously been produced. In this regard, 1,3,5-tris-tert-butylpentalene (K. Hafner and H. U. Suess, *Angew. Chem.*, 1973, 85, 626-627), 1,2-bis(carboxymethyl)-4,6-bis(tert-butyl)pentalene (B. Kitschke and H. J. Lindner, *Tetrahedron. Lett.*, 1977, 2511-2514), 1,3-bis(N,N-dimethylamino)pentalene (K. Hafner, K. F. Bangert and V. Orfanos, *Angew. Chem. Int. Ed. Engl.*, 1967, 6, 451-452), 3-alkyl substituted 1,2-dihydropentalenes (R. Kaiser and K. Hafner, *Angew. Chem. Int. Ed. Engl.*, 1970, 9, 892-893) and 1,4-diamino-3,6-dimethylpentalene-2,6-dicarbonitrile (K. Hartke and R. Matusch, *Angew. Chem. Int. Ed. Engl.*, 1972, 11, 50-51) have been previously obtained.

Metal complexes of various substituted pentalene ligands have also been produced. Alkylated hydropentalenyls have been used to form $Re(\eta^5-Pn^{Me}H)(CO)_3$ from the $TlPn^{Me}H$ salts and $[Re(THF)(CO)_3Br]_2$ (S. C. Jones, P. Roussel, T. Hascall and D. O'Hare, *Organometallics*, 2006, 25, 221-229). $Mo_2(\mu:\eta^5,\eta^5-Pn^{1,4-(iPr3Si)})_2$ has been prepared from the dinuclear $Mo_2(OAc)_4$ and $K_2Pn^{1,4-(iPr3Si)}$ (M. C. Kuchta, F. G. N. Cloke and P. B. Hitchcock, *Organometallics*, 1998, 17, 1934-1936) $M_2(\mu:\eta^5,\eta^5-Pn^{1,4-(iPr3Si)})_2$ (M=Rh, Pd) has also been prepared from $Rh_2(OAc)_4$ and $Pd(\eta^4-COD)Cl_2$ (F. G. N. Cloke, *Pure Appl. Chem.*, 2001, 73, 233-238).

Complexes of $syn-[Fe_2(CO)_4(\mu-CO)](\mu:\eta^5,\eta^5-L)$ (L=$Pn^{1,3-Me}$, $Pn^{1-NMe2}$ or $Pn^{1-Ph}$) have also been made (D. F. Hunt and J. W. Russell, *J. Am. Chem. Soc.*, 1972, 94, 7198-7199; D. F. Hunt and J. W. Russell, *J. Organomet. Chem.*, 1972, 46, C22-C24). $Ta(\eta^8-Pn^{1,5-SiMe3})$ was prepared from the protonolysis reaction of the 1,4-substituted COT derivative $Ta[\eta^8-C_8H_4(SiMe_3)_2]Me_3$ with $[NH^iPr_2Et]Cl$ (Q. A. Abbasali, F. G. N. Cloke, P. B. Hitchcock and S. C. P. Joseph, *Chem Commun.*, 1997, 1541-1542). The sandwich complexes $M(\eta^8-Pn^{1,4-iPr3Si})_2$ have also been prepared (F. Geoffrey, N. Cloke and P. B. Hitchcock, *J. Am. Chem. Soc.*, 1997, 119, 7899-7900; F. G. N. Cloke, J. C. Green and C. N. Jardine, *Organometallics*, 1999, 18, 1080-1086). Isomeric mixtures of 1- and 2-R substituted $Ru_3(CO)_8Pn^{1/2-R}$, $Ru_3(CO)_8Pn^{1,5-SiMe3}$ and $Ru_3(CO)_8Pn^{1,3,5-SiMe3}$ (R=Me, Ph) complexes have also been obtained (A. K. Howard, S. A. R. Knox, F. G. A. Stone, A. C. Szary and P. Woodward, *J. Chem. Soc. Chem. Commun.*, 1974, 788-789; S. A. R. Knox, R. J. McKinney, V. Riera, F. G. A. Stone and A. C. Szary, *J. Chem. Soc. Dalt. Trans.*, 1979, 1801-1811).

The introduction of Pn into complexes usually arises from reaction of $Pn^{2-}$, which originates from $PnH_2$. This can be made by, for example, skeletal transformation using trans-1,2-bis(2,2-dibromocyclopropyl)ethane (U. H. Brinker and I. Fleischhauer, *Angew. Chem.*, 1980, 92, 314-315), LiMe induced Skattebøl rearrangement of 8,8-dibromobicyclo[5.1.0]octa-2,4-diene (M. S. Baird and C. B. Reese, *Tetrahedron. Lett.*, 1976, 2895-2898), or intramolecular cyclisation of 6-(2-aminovinyl)fulvenes and nucleophilic substitution to 1,2-dihydropentalenes (R. Kaiser and K. Hafner, *Angew. Chem.*, 1973, 85, 361-362). However, known solution-phase syntheses of $PnH_2$ are laborious to conduct on a large scale and can suffer from disappointingly low yields either due to side-reactions or to the thermally sensitive nature of the dihydro product.

A pyrolytic method has been developed which uses a closed loop flow system that is regulated by pressure transducers which give a precise and reproducible system (F. G. N. Cloke, M. C. Kuchta, R. M. Harker, P. B. Hitchcock and J. S. Parry, *Organometallics*, 2000, 19, 5795-5798). However whilst this method is chemically simple and elegant, it required the use of highly specialised apparatus, which has a financial and availability disincentive for many laboratories.

With regard to the production of substituted pentalene compounds, and metal complexes of substituted pentalene compounds, the existing preparations are based ultimately upon $Pn^{2-}$; and consequently they suffer from the same drawbacks discussed above. Furthermore, in relation to multiply substituted compounds, there is inflexibility for total substitution using the known routes. Using dianion and electrophilic alkylating/silylating agents followed by double deprotonation, and thus continuing the cycle, will invariably lead to geminal substitution before the six positions could be replaced.

It would therefore be advantageous to provide a new synthetic route to multiply substituted pentalene compounds, in particular hexa-pentalene compounds.

In particular, a technique that uses standard equipment and techniques would be advantageous. A synthesis that is entirely solution-phase, and/or high-yielding and/or facile would be desirable. A bulk-scale process would also be advantageous, so that the chemistry should not be hampered by a restricted availability of the organic component.

There could, consequently, also be provided novel substituted pentalene compounds.

The present invention provides, in a first aspect, a substituted pentalene of formula (I):

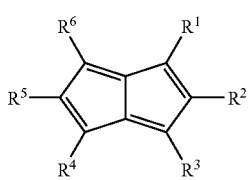

(I)

wherein $R^1$, $R^2$, $R^3$, $R^4$, $R^5$ and $R^6$ are each independently a substituent group having up to 40 carbon atoms, provided that $R^1$, $R^2$, $R^3$, $R^4$, $R^5$ and $R^6$ are not each phenyl.

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms and provided that not all of $R^1$, $R^2$, $R^3$, $R^4$, $R^5$ and $R^6$ are phenyl.

Preferably, not all of $R^1$, $R^2$, $R^3$, $R^4$, $R^5$ and $R^6$ are chloride groups. More preferably, not all of $R^1$, $R^2$, $R^3$, $R^4$, $R^5$ and $R^6$ are halide groups. In one embodiment, none of $R^1$, $R^2$, $R^3$, $R^4$, $R^5$ and $R^6$ are chloride groups. In one embodiment, none of $R^1$, $R^2$, $R^3$, $R^4$, $R^5$ and $R^6$ are halide groups.

In one embodiment, one or more of the $R^1$, $R^2$, $R^3$, $R^4$, $R^5$ and $R^6$ groups are substituent groups that contain at least one hydrogen atom, e.g. two or more, preferably three or more, preferably four or more, such as five or more, e.g. all of the $R^1$, $R^2$, $R^3$, $R^4$, $R^5$ and $R^6$ groups may be substituent groups that contain at least one hydrogen atom.

In one embodiment, each of $R^1$, $R^2$, $R^3$, $R^4$, $R^5$ and $R^6$ may be an organic group.

Each of $R^1$, $R^2$, $R^3$, $R^4$, $R^5$ and $R^6$ may be the same. Alternatively, one or more of these groups may be different (e.g. two or more, three or more, four or more, five or more, or all six of these groups may be different). In one embodiment, there are five or fewer different substituent groups, preferably four or fewer different substituent groups, such as three or fewer different substituent groups, e.g. two or fewer different substituent groups.

In one embodiment, $R^2$ and $R^5$ are the same. The remaining R groups may be the same as $R^2$ and $R^5$, or may be different to $R^2$ and $R^5$. For example, $R^3$ and $R^6$ may be the same as $R^2$ and $R^5$, and/or $R^1$ and $R^4$ may be the same as $R^2$ and $R^5$.

In one embodiment, $R^1$ and $R^4$ are the same. The remaining R groups may be the same as $R^1$ and $R^4$, or may be different to $R^1$ and $R^4$. For example, $R^3$ and $R^6$ may be the same as $R^1$ and $R^4$, and/or $R^2$ and $R^5$ may be the same as $R^1$ and $R^4$.

In one embodiment, $R^3$ and $R^6$ are the same. The remaining R groups may be the same as $R^3$ and $R^6$, or may be different to $R^3$ and $R^6$. For example, $R^1$ and $R^4$ may be the same as $R^3$ and $R^6$, and/or $R^2$ and $R^5$ may be the same as $R^3$ and $R^6$.

Preferably, $R^1$, $R^2$, $R^3$, $R^4$, $R^5$ and $R^6$ are each independently a substituent group having up to 30 carbon atoms, for example up to 24 carbon atoms, more preferably up to 20 carbon atoms, for example up to 16 carbon atoms, most preferably having either no carbon atoms or from 1 to 12 carbon atoms, for example from 1 to 8 carbon atoms, such as 1, 2, 3, 4, 5 or 6 carbon atoms.

Preferably, one or more, such as two or more, more preferably three or more, such as four or more, e.g. five or more, of the $R^1$, $R^2$, $R^3$, $R^4$, $R^5$ and $R^6$ groups are alkyl, aryl, aralkyl, amino (which may, optionally, be mono or di or tert substituted, e.g. with hydrocarbon groups, such as with C1, 2, 3 or 4 alkyl groups), and vinyl groups. These groups may be branched or unbranched.

Preferably, one or more, such as two or more, more preferably three or more, such as four or more, e.g. five or more, of the $R^1$, $R^2$, $R^3$, $R^4$, $R^5$ and $R^6$ groups are alkyl, aryl, aralkyl, and vinyl groups. These groups may be branched or unbranched.

$R^1$, $R^2$, $R^3$, $R^4$, $R^5$ and $R^6$ may, in one embodiment, each independently be selected from alkyl, aryl, aralkyl, amino (which may, optionally, be mono or di or tert substituted, e.g. with hydrocarbon groups, such as with C1, 2, 3 or 4 alkyl groups), and vinyl groups. The groups may be branched or unbranched.

In one embodiment, one or more, such as two or more, more preferably three or more, such as four or more, e.g. five or more, of the $R^1$, $R^2$, $R^3$, $R^4$, $R^5$ and $R^6$ groups are alkyl, aryl and aralkyl groups.

In one embodiment, $R^1$, $R^2$, $R^3$, $R^4$, $R^5$ and $R^6$ are such that there are no heteroatoms attached directly to the pentalenic ring.

For example, $R^1$, $R^2$, $R^3$, $R^4$, $R^5$ and $R^6$ may each independently be selected from alkyl, aryl and aralkyl groups.

In one embodiment, $R^1$, $R^3$, $R^4$, and $R^6$ are not aromatic groups.

In one embodiment, $R^1$, $R^3$, $R^4$, and $R^6$ may each independently be selected from unbranched or branched C1-12 alkyl groups (more preferably unbranched or branched C1-8 alkyl, most preferably unbranched or branched C1-4 alkyl, e.g. unbranched C1-4 alkyl). For example, $R^1$, $R^3$, $R^4$, and $R^6$ may each independently be selected from methyl, ethyl, n-propyl, i-propyl, s-butyl, t-butyl and n-butyl groups.

In one embodiment, $R^2$ and $R^5$ may each independently be selected from unbranched or branched C1-12 alkyl groups (more preferably unbranched or branched C1-8 alkyl, such as unbranched or branched C1-4 alkyl, e.g. unbranched C1-4 alkyl) and C6-C12 aryl groups. For example, $R^2$ and $R^5$ may each independently be selected from methyl, ethyl, n-propyl, i-propyl, s-butyl, t-butyl, n-butyl, n-pentyl and phenyl groups.

In one embodiment, each of $R^1$, $R^2$, $R^3$, $R^4$, $R^5$ and $R^6$ is a methyl group. This compound of formula (I) may be referred to as Pn*.

The present invention provides, in a second aspect, a substituted pentalene of formula (Ia):

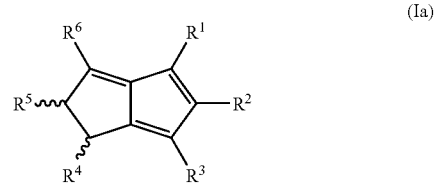

(Ia)

wherein $R^1$, $R^2$, $R^3$, $R^4$, $R^5$ and $R^6$ are each independently a substituent group having up to 40 carbon atoms.

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. In one embodiment, each of $R^1$, $R^2$, $R^3$, $R^4$, $R^5$ and $R^6$ may be an organic group.

Preferably, not all of $R^1$, $R^2$, $R^3$, $R^4$, $R^5$ and $R^6$ are chloride groups. More preferably, not all of $R^1$, $R^2$, $R^3$, $R^4$, $R^5$ and $R^6$ are halide groups. In one embodiment, none of $R^1$, $R^2$, $R^3$, $R^4$, $R^5$ and $R^6$ are chloride groups. In one embodiment, none of $R^1$, $R^2$, $R^3$, $R^4$, $R^5$ and $R^6$ are halide groups.

In one embodiment, one or more of the $R^1$, $R^2$, $R^3$, $R^4$, $R^5$ and $R^6$ groups are substituent groups that contain at least one hydrogen atom, e.g. two or more, preferably three or more, preferably four or more, such as five or more, e.g. all of the $R^1$, $R^2$, $R^3$, $R^4$, $R^5$ and $R^6$ groups may be substituent groups that contain at least one hydrogen atom.

Each of $R^1$, $R^2$, $R^3$, $R^4$, $R^5$ and $R^6$ may be the same. Alternatively, one or more of these groups may be different (e.g. two or more, three or more, four or more, five or more, or all six of these groups may be different). In one embodiment, there are five or fewer different substituent groups, preferably four or fewer different substituent groups, such as three or fewer different substituent groups, e.g. two or fewer different substituent groups.

In one embodiment, $R^2$ and $R^5$ are the same. The remaining R groups may be the same as $R^2$ and $R^5$, or may be different to $R^2$ and $R^5$. For example, $R^3$ and $R^6$ may be the same as $R^2$ and $R^5$, and/or $R^1$ and $R^4$ may be the same as $R^2$ and $R^5$.

In one embodiment, $R^1$, $R^3$, $R^4$ and $R^6$ are the same. The remaining R groups may be the same as $R^1$, $R^3$, $R^4$ and $R^6$, or may be different to $R^1$, $R^3$, $R^4$ and $R^6$.

Preferably, $R^1$, $R^2$, $R^3$, $R^4$, $R^5$ and $R^6$ are each independently a substituent group having up to 30 carbon atoms, for example up to 24 carbon atoms, more preferably up to 20 carbon atoms, for example up to 16 carbon atoms, most preferably having either no carbon atoms or from 1 to 12 carbon atoms, for example from 1 to 8 carbon atoms, such as 1, 2, 3, 4, 5 or 6 carbon atoms.

Preferably, one or more, such as two or more, more preferably three or more, such as four or more, e.g. five or more, of the $R^1$, $R^2$, $R^3$, $R^4$, $R^5$ and $R^6$ groups are alkyl, aryl, aralkyl, amino (which may, optionally, be mono or di or tert substituted, e.g. with hydrocarbon groups, such as with C1, 2, 3 or 4 alkyl groups), and vinyl groups. These groups may be branched or unbranched.

Preferably, one or more, such as two or more, more preferably three or more, such as four or more, e.g. five or more, of the $R^1$, $R^2$, $R^3$, $R^4$, $R^5$ and $R^6$ groups are alkyl, aryl, aralkyl, and vinyl groups. These groups may be branched or unbranched.

$R^1$, $R^2$, $R^3$, $R^4$, $R^5$ and $R^6$ may, in one embodiment, each independently be selected from alkyl, aryl, aralkyl, amino (which may, optionally, be mono or di or tert substituted, e.g. with hydrocarbon groups, such as with C1, 2, 3 or 4 alkyl groups), and vinyl groups. The groups may be branched or unbranched. For example, $R^1$, $R^2$, $R^3$, $R^4$, $R^5$ and $R^6$ may each independently be selected from alkyl, aryl and aralkyl groups.

In one embodiment, $R^1$, $R^3$, $R^4$, and $R^6$ are not aromatic groups.

In one embodiment, one or more, such as two or more, more preferably three or more, such as four or more, e.g. five or more, of the $R^1$, $R^2$, $R^3$, $R^4$, $R^5$ and $R^6$ groups are alkyl, aryl and aralkyl groups.

In one embodiment, $R^1$, $R^2$, $R^3$, $R^4$, $R^5$ and $R^6$ are such that there are no heteroatoms attached directly to the pentalenic ring.

In one embodiment, $R^1$, $R^3$, $R^4$, and $R^6$ may each independently be selected from unbranched or branched C1-12 alkyl groups (more preferably unbranched or branched C1-8 alkyl, most preferably unbranched or branched C1-4 alkyl, e.g. unbranched C1-4 alkyl). For example, $R^1$, $R^3$, $R^4$, and $R^6$ may each independently be selected from methyl, ethyl, n-propyl, i-propyl, s-butyl and n-butyl groups.

In one embodiment, $R^2$ and $R^5$ may each independently be selected from unbranched or branched C1-12 alkyl groups (more preferably unbranched or branched C1-8 alkyl, such as unbranched or branched C1-4 alkyl, e.g. unbranched C1-4 alkyl) and C6-C12 aryl groups. For example, $R^2$ and $R^5$ may each independently be selected from methyl, ethyl, n-propyl, i-propyl, s-butyl, n-butyl, n-pentyl and phenyl groups.

In one embodiment, each of $R^1$, $R^2$, $R^3$, $R^4$, $R^5$ and $R^6$ is a methyl group. This compound of formula (Ia) may be referred to as 1,2-Pn*$H_2$.

The present invention provides, in a third aspect, a substituted pentalene of formula (Ib):

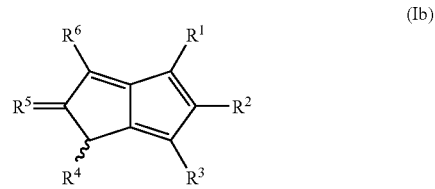

(Ib)

wherein $R^1$, $R^2$, $R^3$, $R^4$, $R^5$ and $R^6$ are each independently a substituent group having up to 40 carbon atoms.

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. In one embodiment, each of $R^1$, $R^2$, $R^3$, $R^4$, $R^5$ and $R^6$ may be an organic group.

Preferably, not all of $R^1$, $R^2$, $R^3$, $R^4$, $R^5$ and $R^6$ are chloride groups. More preferably, not all of $R^1$, $R^2$, $R^3$, $R^4$, $R^5$ and $R^6$ are halide groups. In one embodiment, none of $R^1$, $R^2$, $R^3$, $R^4$, $R^5$ and $R^6$ are chloride groups. In one embodiment, none of $R^1$, $R^2$, $R^3$, $R^4$, $R^5$ and $R^6$ are halide groups.

In one embodiment, one or more of the $R^1$, $R^2$, $R^3$, $R^4$, $R^5$ and $R^6$ groups are substituent groups that contain at least one hydrogen atom, e.g. two or more, preferably three or more, preferably four or more, such as five or more, e.g. all of the $R^1$, $R^2$, $R^3$, $R^4$, $R^5$ and $R^6$ groups may be substituent groups that contain at least one hydrogen atom.

Each of $R^1$, $R^2$, $R^3$, $R^4$, $R^5$ and $R^6$ may be the same. Alternatively, one or more of these groups may be different (e.g. two or more, three or more, four or more, five or more, or all six of these groups may be different). In one embodiment, there are five or fewer different substituent groups, preferably four or fewer different substituent groups, such as three or fewer different substituent groups, e.g. two or fewer different substituent groups.

In one embodiment, $R^2$ and $R^5$ are the same. The remaining R groups may be the same as $R^2$ and $R^5$, or may be different to $R^2$ and $R^5$. For example, $R^3$ and $R^6$ may be the same as $R^2$ and $R^5$, and/or $R^1$ and $R^4$ may be the same as $R^2$ and $R^5$.

In one embodiment, $R^1$, $R^3$, $R^4$ and $R^6$ are the same. The remaining R groups may be the same as $R^1$, $R^3$, $R^4$ and $R^6$, or may be different to $R^1$, $R^3$, $R^4$ and $R^6$.

Preferably, $R^1$, $R^2$, $R^3$, $R^4$, $R^5$ and $R^6$ are each independently a substituent group having up to 30 carbon atoms, for example up to 24 carbon atoms, more preferably up to 20 carbon atoms, for example up to 16 carbon atoms, most preferably having either no carbon atoms or from 1 to 12 carbon atoms, for example from 1 to 8 carbon atoms, such as 1, 2, 3, 4, 5 or 6 carbon atoms.

Preferably, one or more, such as two or more, more preferably three or more, such as four or more, e.g. five or more, of the $R^1$, $R^2$, $R^3$, $R^4$, $R^5$ and $R^6$ groups are alkyl, aryl, aralkyl, amino (which may, optionally, be mono or di or tert substituted, e.g. with hydrocarbon groups, such as with C1, 2, 3 or 4 alkyl groups), and vinyl groups. These groups may be branched or unbranched.

Preferably, one or more, such as two or more, more preferably three or more, such as four or more, e.g. five or more, of the $R^1$, $R^2$, $R^3$, $R^4$, $R^5$ and $R^6$ groups are alkyl, aryl, aralkyl, and vinyl groups. These groups may be branched or unbranched.

$R^1$, $R^2$, $R^3$, $R^4$, $R^5$ and $R^6$ may, in one embodiment, each independently be selected from alkyl, aryl, aralkyl, amino (which may, optionally, be mono or di or tert substituted, e.g. with hydrocarbon groups, such as with C1, 2, 3 or 4 alkyl groups), and vinyl groups. The groups may be branched or unbranched. For example, $R^1$, $R^2$, $R^3$, $R^4$, $R^5$ and $R^6$ may each independently be selected from alkyl, aryl and aralkyl groups.

In one embodiment, $R^1$, $R^3$, $R^4$, and $R^6$ are not aromatic groups.

In one embodiment, one or more, such as two or more, more preferably three or more, such as four or more, e.g. five or more, of the $R^1$, $R^2$, $R^3$, $R^4$, $R^5$ and $R^6$ groups are alkyl, aryl and aralkyl groups.

In one embodiment, $R^1$, $R^2$, $R^3 R^4$, $R^5$ and $R^6$ are such that there are no heteroatoms attached directly to the pentalenic ring.

In one embodiment, $R^1$, $R^3$, $R^4$, and $R^6$ may each independently be selected from unbranched or branched C1-12 alkyl groups (more preferably unbranched or branched C1-8 alkyl, most preferably unbranched or branched C1-4 alkyl, e.g. unbranched C1-4 alkyl). For example, $R^1$, $R^3$, $R^4$, and $R^6$ may each independently be selected from methyl, ethyl, n-propyl, i-propyl, s-butyl and n-butyl groups.

In one embodiment, $R^2$ and $R^5$ may each independently be selected from unbranched or branched C1-12 alkyl groups (more preferably unbranched or branched C1-8 alkyl, such as unbranched or branched C1-4 alkyl, e.g. unbranched C1-4 alkyl) and C6-C12 aryl groups. For example, $R^2$ and $R^5$ may each independently be selected from methyl, ethyl, n-propyl, i-propyl, s-butyl, n-butyl, n-pentyl and phenyl groups.

Preferably, $R^5$ is an alkyl group.

In one embodiment, each of $R^1$, $R^2$, $R^3$, $R^4$, $R^5$ and $R^6$ is a methyl group. This compound of formula (Ib) may be referred to as Pn*'.

The present invention provides, in a fourth aspect, a substituted pentalene of formula (Ic):

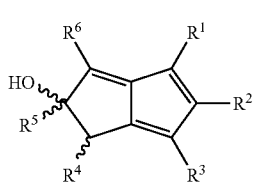

(Ic)

wherein $R^1$, $R^2$, $R^3$, $R^4$, $R^5$ and $R^6$ are each independently a substituent group having up to 40 carbon atoms.

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the third aspect above.

In one embodiment, each of $R^1$, $R^2$, $R^3$, $R^4$, $R^5$ and $R^6$ is a methyl group. This compound of formula (Ic) may be referred to as Pn*($H_2O$).

The present invention provides, in a fifth aspect, a substituted pentalene of formula (Id):

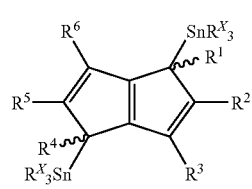

(Id)

wherein $R^x$, $R^1$, $R^2$, $R^3$, $R^4$, $R^5$ and $R^6$ are each independently a substituent group having up to 40 carbon atoms.

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the third aspect above.

Each $R^x$ may be any substituent group (i.e. a group that substitutes a hydrogen group on a carbon atom), provided that it has no more than 40 carbon atoms. Preferably each $R^x$ is the same.

In one embodiment, each $R^x$ may be a branched or unbranched C1-12 alkyl group (more preferably branched or unbranched C1-8 alkyl, e.g. C1-6 branched or unbranched alkyl, most preferably C1, 2, 3 or 4 unbranched alkyl), or a C1-4 alkoxy group.

In one embodiment, each of $R^x$, $R^2$, $R^3$, $R^4$, $R^5$ and $R^6$ is a methyl group. This compound of formula (Id) may be referred to as Pn*$(SnMe_3)_2$.

The present invention provides, in a sixth aspect, a substituted pentalene of formula (Ie):

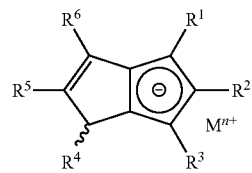

(Ie)

wherein $R^1$, $R^2$, $R^3$, $R^4$, $R^5$ and $R^6$ are each independently a substituent group having up to 40 carbon atoms, M is an alkali or alkaline earth metal and n represents the valency of the metal M.

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the third aspect above.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

In one embodiment, each of $R^1$, $R^2$, $R^3$, $R^4$, $R^5$ and $R^6$ is a methyl group and M is Li. This compound of formula (Ie) may be referred to as LiPn*H.

The present invention provides, in a seventh aspect, a substituted pentalene of formula (If):

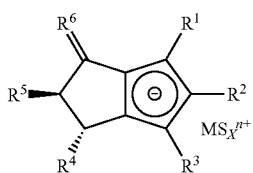

(If)

wherein $R^1$, $R^2$, $R^3$, $R^4$, $R^5$ and $R^6$ are each independently a substituent group having up to 40 carbon atoms, M is an alkali or alkaline earth metal and n represents the valency of the metal M, S is a chelating solvent, and X is a number from 0 to 10.

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the second aspect above.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

S may be any chelating solvent. In one embodiment, S is dimethoxyethane (DME), N,N,N',N'-tetramethylethylenediamine (TMEDA) or tetrahydrofuran (THF). Preferably, S is DME.

X may, for example, be from 0 to 8, such as from 0.1 to 7, e.g. 0.2 to 6.

In one embodiment, X is from 0 to 1, e.g. from 0 to 0.8, such as from 0.1 to 0.6, more preferably from 0.1 to 0.5, such as from 0.1 to 0.4, most preferably from 0.2 to 0.3.

In one embodiment, each of $R^1$, $R^2$, $R^3$, $R^4$, $R^5$ and $R^6$ is a methyl group, M is Li and S is DME. This compound of formula (If) may be referred to as Li(Pn*'H)(DME)$_x$.

The present invention provides, in an eighth aspect, a substituted pentalene of formula (Ig):

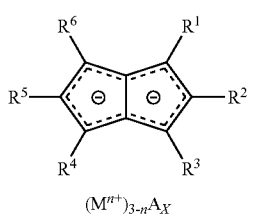

(Ig)

wherein $R^1$, $R^2$, $R^3$, $R^4$, $R^5$ and $R^6$ are each independently a substituent group having up to 40 carbon atoms, M is an alkali or alkaline earth metal and n represents the valency of the metal M, A is a tertiary amine and X is a number from 0 to 10.

A may be any tertiary amine. Preferably, A is a tertiary diamine. In one embodiment, A is tetraethylethylenediamine, tetramethylpropanediamine or tetramethylethanediamine. Preferably, A is N,N,N',N'-tetramethyl-ethane-1,2-diamine (TMEDA).

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the third aspect above.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

X may, for example, be from 0 to 8, such as from 0.1 to 7, e.g. 0.15 to 6.

In one embodiment, X is from 0 to 0.75, such as from 0.05 to 0.6, more preferably from 0.1 to 0.5, such as from 0.1 to 0.4, e.g. from 0.15 to 0.3, most preferably from 0.15 to 0.25.

In an alternative embodiment, X may be from 1 to 2, such as from 1.5 to 2, e.g. about 2.

In one embodiment, each of $R^1$, $R^2$, $R^3$, $R^4$, $R^5$ and $R^6$ is a methyl group, M is Li and A is TMEDA. This compound of formula (Ig) may be referred to as Li$_2$Pn*(TMEDA)$_x$.

The present invention provides, in a ninth aspect, a metal complex, which is a complex of one or more metal atoms or ions with one or more ligands, wherein one or more of the ligands comprises a compound of formula (I), (Ia), (Ib), (Ic) or (Id) as defined above.

The preferred features in relation to the groups $R^1$, $R^2$, $R^3$, $R^4$, $R^5$ and $R^6$ in the ligands that comprise a compound of formula (I), (Ia), (Ib), (Ic) or (Id) are the same as described in the first to fifth aspects above.

In one embodiment, one or more of the ligands comprise a compound which is Pn*, 1,2 Pn*H$_2$, Pn*', Pn*(H$_2$O), Pn*(SnMe$_3$)$_2$, LiPn*H, Li(Pn*'H)(DME)$_x$, or Li$_2$Pn* (TMEDA)$_x$.

Preferably, the metal complex is an organometallic catalyst.

In one embodiment, the ligand may be a compound of formula (I), (Ia), (Ib), (Ic) or (Id).

In an alternative embodiment, the ligand may comprise two or more compounds of formula (I), (Ia), (Ib), (Ic) or (Id) coupled together. For example, the ligand may comprise two compounds of formula (I), (Ia), (Ib), (Ic) or (Id) coupled together via their $R^5$ groups. The two $R^5$ groups, may, for example, together form a linking group $R_wE_n$, wherein R is an organic group having up to 40 carbon atoms, E is a Group 13-16 element, W is an integer and n is an integer.

When there is more than one R group, each R may be the same or different.

R may, for example, be an alkyl, aryl, alkenyl or alkaryl group.

R may, preferably, have up to 30 carbon atoms, for example up to 24 carbon atoms, more preferably up to 20 carbon atoms, for example up to 16 carbon atoms, most preferably from 1 to 12 carbon atoms, for example from 1 to 8 carbon atoms, such as 1, 2, 3, 4, 5 or 6 carbon atoms.

E may be any Group 13-16 element, for example E may be B, Si, N, P, O or S.

When there is more than one E group, each E may be the same or different.

W may, for example, be an integer from 1 to 4, such as 1, 2 or 3.

n may, for example, be an integer from 1 to 4, such as 1, 2 or 3.

Examples of such complexes include:
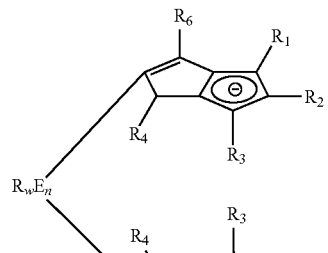
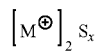
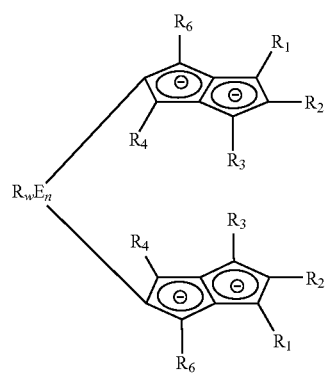
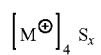
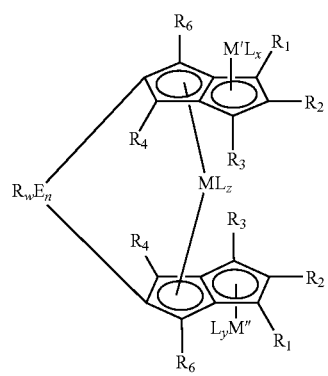
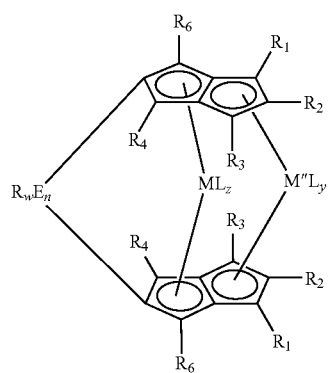
-continued
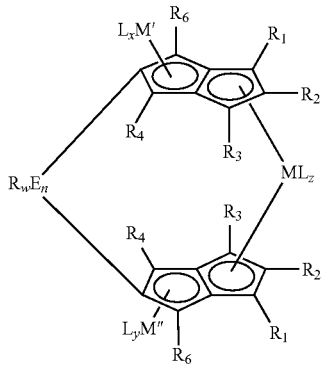
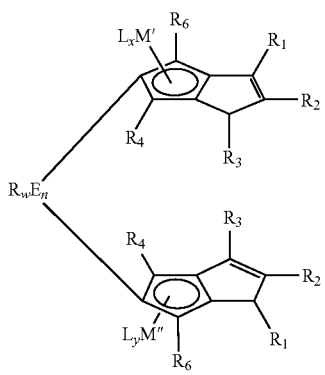
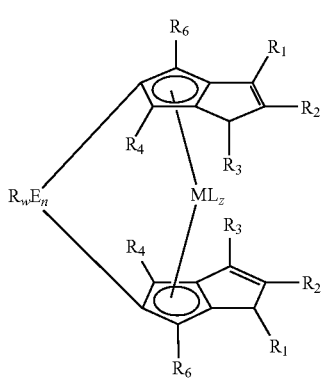
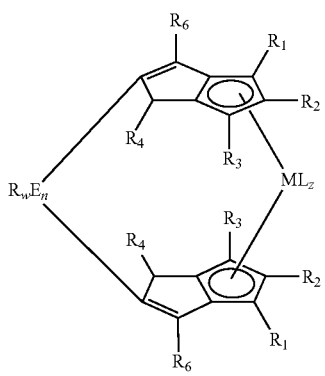

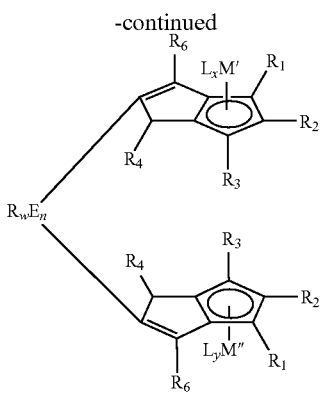

where R, E, W, n, are as defined above, M, M' and M" are each independently a metal atom or ion, L is a ligand, S is a chelating solvent, x, y and z are integers, and $R^1$, $R^2$, $R^3$, $R^4$ and $R^6$ are as defined above in relation to formulae (I), (Ia), (Ib), (Ic) or (Id).

S may, for example, be dimethoxyethane (DME), N,N,N', N'-tetramethylethylenediamine (TMEDA) or tetrahydrofuran (THF).

When there is more than one ligand L, each may be the same or different. Each L may be a monodonor ligand, bidentate ligand or polydentate ligand.

x, y and z may suitably be integers from 0 to 6, such as 1, 2, 3 or 4.

Preferred metals M, M' and M" are as defined above.

In one embodiment, the metal complex is a complex of a single metal atom or ion with one or more ligands. Alternatively, the metal complex may be a complex of a two or more metal atoms or ions with one or more ligands. In this case, the metal atoms or ions are preferably the same.

There may be two or more ligands in the complex, for example three, four, five, six, seven, eight or more ligands.

In one embodiment, all of the ligands are ligands that comprise compounds in accordance with formula (I), (Ia), (Ib), (Ic) or (Id).

In alternative embodiment, the metal complex may include one or more ligands (e.g. two three, four, five or more ligands) that are not ligands that comprise compounds of formula (I), (Ia), (Ib), (Ic) or (Id). The complex may include one or more ligands selected from monodonor ligands, bidentate ligands and polydentate ligands that are not in accordance with formula (I), (Ia), (Ib), (Ic) or (Id).

In one embodiment, the complex may include one or more functional groups as well as the one or more ligands in accordance with formula (I), (Ia), (Ib), (Ic) or (Id). These functional groups may, for example, be selected from carbonyl groups, alkyl groups (e.g. C1-12 straight or branched alkyl, such as C1-8 straight or branched alkyl, e.g. C1-4 straight or branched alkyl), halide groups (such as F, Cl, or Br), hydride groups, borohydride groups and hydrocarbon ring groups (e.g. aromatic ring groups, including cyclopentadienyl). There may, for example, be two, three, four, five or more of these groups. When there are two or more of these groups, they may be the same or different.

The metal may be any metal atom or ion, for example it may be a transition metal (d block metal) or a lanthanide or actinide (f block metal). It may also be an alkali or alkaline earth metal (s block metal) or a p block metal (e.g. Group 13 or 14 metal).

In one embodiment, it may be a transition metal (d block) atom or ion. It may be a Group 3, 4 or 5 transition metal, e.g. Sc, Y, Ti, Zr, Hf, V. It may be a Group 8, 9 or 10 transition metal, e.g. Fe, Ru, Co, Rh, Ir, Ni, Pd, Pt.

Other transition metals that can be used include Group 6 metals, such as Cr and Mo, Group 7 metals, such as Mn and Re, and Group 11 and 12 metals such as Cu and Zn.

The metal may be a lanthanide metal atom or ion, e.g. La, Ce, Pr, Nd, Lu.

The metal may also be selected from the actinides, such as Th and U, alkali metals, e.g. K, alkaline earth metals, e.g. Mg and Ca, and Group 13 and 14 metals such as Ga and Ge.

The metal may bind to the or each ligand comprising formula (I), (Ia), (Ib), (Ic) or (Id) via one or more carbon atom in the ring structure. For example, the metal may bind to the or each ligand comprising formula (I), (Ia), (Ib), (Ic) or (Id) via two or more carbon atoms in the ring structure, such as three, four, five, six, seven or eight carbons in the ring structure.

Overall the complex may be neutral or may be positively or negatively charged.

The metal complex may be of formula $M_A L_B G_C$ wherein M is a metal, L is a ligand comprising a compound of formula (I), (Ia), (Ib), (Ic) or (Id) as defined above, G is a functional group, A is 1, 2, 3 or 4, B is 1, 2, 3 or 4, and C is 0, 1, 2, 3, 4, 5, 6, 7 or 8.

The metal M may be any metal atom or ion, for example it may be a transition metal (d block metal) or a lanthanide or actinide (f block metal). It may also be an alkali or alkaline earth metal (s block metal) or a p block metal (e.g. Group 13 or 14 metal). Preferred metals are as discussed above.

The functional group may be as discussed above; when there is more than one functional group these may be the same or different. The functional group may in particular be selected from carbonyl groups, halide groups (such as F, Cl, or Br), and hydrocarbon ring groups (e.g. aromatic ring groups, including cyclopentadienyl).

The ligand L may, in one embodiment, be a compound of formula (I), (Ia), (Ib), (Ic) or (Id) as defined above. The preferred features in relation to the groups $R^1$, $R^2$, $R^3$, $R^4$, $R^5$ and $R^6$ in the compounds of formula (I), (Ia), (Ib), (Ic) or (Id) are the same as described in the first to fifth aspects above.

In one embodiment, the ligand L is a compound which is Pn*, 1,2Pn*$H_2$, Pn*', Pn*($H_2O$), Pn*($SnMe_3$)$_2$, LiPn*H, Li(Pn*'H)(DME)$_x$, or Li$_2$Pn*(TMEDA)$_x$.

Preferably A is 1, 2 or 4. Preferably B is 1 or 2. Preferably C is 0, 2, 3, 4, 5, 6 or 8.

Examples of metal complexes in accordance with the invention include: Ce($\eta^8$-Pn*)$_2$, [Ti($\eta^8$-Pn*)Cl($\mu$-Cl)]$_2$, Zr(Cp)($\eta^8$-Pn*)Cl, [Co(CO)$_2$]$_2$($\mu$:$\eta^5$, $\eta^5$-Pn*), [Fe$_2$(CO)$_4$($\mu$-CO)]($\mu$:$\eta^5$, $\eta^5$-Pn*), [($\eta^8$-Pn*)Ti]$_2$($\mu$-Cl)$_3$, [($\mu$:$\eta^5$, $\eta^3$-Pn*) Rh$_2$(CO)$_2$]$_2$($\mu$-CO)$_2$, Mn$_2$Pn*$_2$, Co$_2$Pn*$_2$, anti-[($\mu$:$\eta^5$, $\eta^1$)-Pn*][Re(CO)$_3$][Re(CO)$_5$], and anti-[($\mu$:$\eta^5$, $\eta^5$)-Pn*][Re(CO)$_3$]$_2$.

The present invention also provides, in a tenth aspect, the use of a complex in accordance with the ninth aspect as a catalyst.

The catalyst may be used to catalyse an organic transformation. The organic transformation may be selected from hydrogenation (for example hydrogenation of carbon-carbon double bond or hydrogenation of carbon-heteroatom double bonds), including the Fischer-Tropsch process in which carbon monoxide is hydrogenated, hydroformylation, hydrosilylation, hydro amination, C—H bond activation (for example alkane C—H activation), C—C bond formation, cyclotrimerisation (for example cyclotrimerisation of alkenes), oxidation, epoxidation, dihydroxylation, and cycloadditions (e.g. [2+2+2] cycloadditions of diynes and isocyanates). The catalyst may be used as an electron transfer medium.

The catalyst may be used to catalyse a polymerisation. The polymerisation may be selected from, for example, olefinic polymerisation (e.g. the production of vinyl polymers), such as α-olefin polymerisation, and polymerisation of polar monomers (e.g. the polymerisation of caprolactone).

In one embodiment, the complex is a Group 8, 9 or 10 metal complex, e.g. a Group 9 metal complex, and is used to catalyse a hydrogenation or hydroformylation reaction. For example, the complex may be a Co, Fe or Rh complex. In one embodiment, a Co or Fe complex may be used as a Fischer-Tropsch catalyst.

In another embodiment, the complex is a Group 3, 4 or 5 metal complex, e.g. a Group 4 metal complex, and is used to catalyse an olefin polymerisation reaction, such as an α-olefin polymerisation. For example, the complex may be a Ti, Hf or Zr complex.

In another embodiment, the complex is a Group 8, 9 or 10 metal complex, e.g. a Group 9 metal complex, and is used to catalyse an olefin polymerisation reaction, such as an α-olefin polymerisation. For example, the complex may be a Co, Fe or Rh complex.

In another embodiment, the complex is a lanthanide metal complex and is used to catalyse a polar monomer polymerisation reaction or an olefin polymerisation reaction. For example, the complex may be a La, Ce or Pr complex.

In another embodiment, the complex is a Group 3 or lanthanide metal complex and is used to catalyse a C—H bond activation reaction. For example, the complex may be a Sc, Y or Lu complex.

In another embodiment, the complex is a Group 7, 8 or 9 metal complex, e.g. a Group 9 metal complex, and is used to catalyse a C—H bond activation reaction. For example, the complex may be a Re, Co, Fe or Rh complex.

In another embodiment, the complex is a Group 8, 9 or 10 metal complex, e.g. a Group 9 metal complex, and is used to catalyse a cyclotrimerisation or cycloaddition reaction. For example, the complex may be a Co or Rh complex.

In another embodiment, the complex is a Group 7, 8 or 9 metal complex, e.g. a Group 9 metal complex, and is used as an electron transfer material. For example, the complex may be a Co or Mn complex.

The present invention provides, in an eleventh aspect, a process for producing a substituted pentalene of formula (Ia):

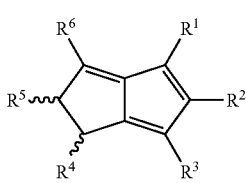
(Ia)

wherein $R^1$, $R^2$, $R^3$, $R^4$, $R^5$ and $R^6$ are each independently a substituent group having up to 40 carbon atoms, the process comprising the following steps:
(a) providing a compound of formula (II):

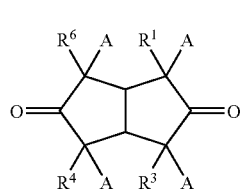
(II)

wherein $R^1$, $R^3$, $R^4$ and $R^6$ are each independently a substituent group having up to 40 carbon atoms and A is a carboxylate group;

(b) reacting the compound of formula (II) with acid to obtain a compound of formula (III):

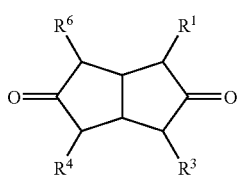
(III)

(c) oxidising the compound of formula (III) to obtain a compound of formula (IV):

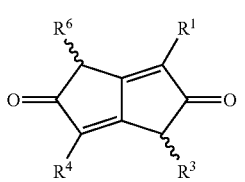
(IV)

(d) reducing of the compound of formula (IV) to obtain a compound of formula (V):

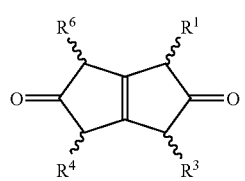
(V)

(e) reacting the compound of formula (V) with a source of $R^2$ and $R^5$ to obtain a compound of formula (VI):

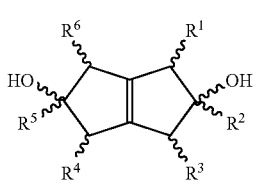
(VI)

(f) dehydrating the compound of formula (VI) to obtain a compound of formula (Ia).

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the second aspect above.

Preferably, $R^1$, $R^2$, $R^3$, $R^4$, $R^5$ and $R^6$ are the same.

Preferably, A is a carboxylate group COOR', where R' is hydrogen or C1-8 branched or unbranched alkyl, for example R' may be hydrogen or C1-4 branched or unbranched alkyl, such as methyl, ethyl or n-propyl.

In one embodiment, step (a) comprises the steps of:
(a1) providing a compound of formula (IIa):

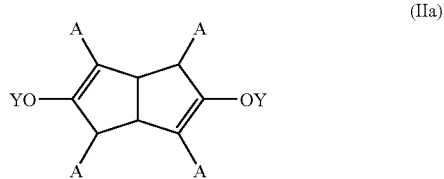

wherein A is a carboxylate group, and Y is hydrogen or C1-8 alkyl;
(a2) reacting the compound of formula (IIa) with a base and a source of $R^1$, $R^3$, $R^4$ and $R^6$ to provide a compound of formula (II).

Preferred options for carboxylate group A are as given above.

Preferably, Y is hydrogen or C1-8 unbranched alkyl, more preferably hydrogen or C1-4 unbranched alkyl, for example methyl, ethyl or n-propyl.

Preferably, the base used in step (a2) is a mild base, for example a base with a pKa (as measured at 25° C.) of from 4 to 13, such as from 6 to 13, more preferably from 7 to 12. Examples of bases include inorganic bases, such as disodium hydrogenphosphate, sodium borate, sodium carbonate, potassium carbonate, and sodium acetate. Preferably, the base is potassium carbonate.

The base used in step (a2) is suitably used in a solvent, in particular an aprotic solvent, such as a dipolar aprotic solvent. For example, the solvent may be acetone, ethyl acetate, DMSO, or DMF.

The source of $R^1$, $R^3$, $R^4$ and $R^6$ may be any suitable source. The source of $R^1$, $R^3$, $R^4$ and $R^6$ may generally be represented as RX, where R is $R^1$, $R^3$, $R^4$ or $R^6$ and X is a leaving group. RX may contain a pendant heteroatom donor (e.g. $ICH_2CH_2CH_2L$ where L is NR2, PR, OR or SR).

In one embodiment, the source of $R^1$, $R^3$, $R^4$ and $R^6$ is a halide thereof, such as the bromine or iodine thereof.

In a preferred embodiment, $R^1$, $R^3$, $R^4$ and $R^6$ are the same and therefore only a single source is required.

In one embodiment, step (a2) is carried out under reflux. The reaction in step (a2) may be continued for any suitable length of time, for example 12 hours or more, such as 24 hours or more, e.g. 48 hours or more.

In step (a2), the molar ratio of the base and source of $R^1$, $R^3$, $R^4$ and $R^6$ to the compound of formula (IIa) may be 3:1 or more, such as 4:1 or more, preferably 5:1 or more, such as 6:1 or more, more preferably 7:1 or more, such as 8:1 or more, most preferably 9:1 or more.

In step (b), the acid may be any suitable acid provided that it is non-oxidising towards the compound of formula (II). Preferably, the acid is a non-oxidant. Preferably, the acid is a strong acid, for example an acid with a pKa (as measured at 25° C.) of 3 or lower, such as 2 or lower, preferably 1 or lower, for example from −6 to 0. Examples of acids that can be used include inorganic acids such as HX, where X=Cl, Br or I, and organic acids such as triflic acid or trifluoroacetic acid. Preferably, the acid is hydrochloric acid.

In step (b), the reaction may suitably be carried out under reflux. The reaction may be carried out in aqueous solution. The reaction in step (b) may be continued for any suitable length of time, for example 24 hours or more, such as 48 hours or more, e.g. 72 hours or more.

In step (c), the oxidising agent may be any suitable agent. The oxidising agent may, preferably, be selected from chlorine, bromine, potassium permanganate, or potassium dichromate. In one embodiment, the oxidising agent is bromine.

Preferably, the oxidising agent is added to the compound of formula (III) in a molar ratio of 2:1 or more, more preferably 2.5:1 or more.

Step (c) is preferably carried out in solution, for example in a non-aqueous solution, such as in methanol or ethanol.

Step (d) may involve the use of any suitable reducing agent. The reducing agent may comprise a metal, for example platinum, palladium, rhodium or zinc. The reducing agent may suitably comprise zinc, for example it may be selected from: zinc dust in THF/AcOH, zinc dust in pyridine/AcOH, and zinc dust in pyridine/THF/AcOH.

Step (d) may be carried out in any suitable solvent system and under any suitable conditions. Preferably, step (d) is carried out at low temperature, for example at 0° C. or lower, such as −5° C. or lower, preferably −10° C. or lower.

Step (e) may use metal halides (e.g. Grignard reagents) or oranolithium compounds as the source of $R^2$ and $R^5$. For example, metal halide compounds of formula $RMX_2$ where R is $R^2$ or $R^5$, M is a metal and X is a halide) may be used. M may in particular be a transition metal, e.g. Mn, or a lanthanide, e.g. Ce. In a preferred embodiment, step (e) uses cerium chloride compounds ($RCeCl_2$ where R is $R^2$ or $R^5$) as the source of $R^2$ and $R^5$. In a preferred embodiment, $R^2$ and $R^5$ are the same and therefore only a single source is required.

Step (e) may be carried out in a solvent, for example a non-aqueous solvent such as THF, TMEDA or $Et_2O$.

Preferably, step (e) is carried out at low temperature, for example at 0° C. or lower, such as −20° C. or lower, preferably −40° C. or lower, such as −60° C. or lower, e.g. −70° C. or lower.

Preferably, in step (e) the source of $R^2$ and $R^5$ is stirred. Preferably the compound of formula (V) is added into the vortex of stirring, most preferably the compound of formula (V) is added dropwise into the vortex of stirring.

Step (f) may use any suitable dehydrating agent. Preferably, a protic dehydrating agent is used, in particular a strong dehydrating agent.

Dehydrating agents may be selected from acids such as p-toluenesulfonic acid, methanesulfonic acid, trifluoroacetic acid, sulfuric acid, hydrochloric acid, perchloric acid, and mixtures thereof. Dehydrating agents may also be selected from acid anhydrides such as acetic anhydride, trifluoroacetic anhydride, trifluoromethanesulfonic anhydride, and mixtures thereof. A preferred agent is sulphuric acid.

Preferably, after dehydration with an acidic dehydrating agent, the product is treated with a base. The base may, for example, be sodium carbonate or potassium carbonate.

Preferably, in step (f) the compound of formula (VI) is added to the dehydrating agent. In particular, the compound of formula (VI) may be added slowly, for example dropwise, to the dehydrating agent.

In step (f) the compound of formula (VI) may be provided in solution, for example non-aqueous solution, such as dichloromethane or trichloromethane.

In a twelfth aspect, the invention provides a process for the production of a substituted pentalene of formula (Ic):

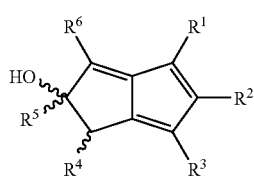

wherein $R^1$, $R^2$, $R^3$, $R^4$, $R^5$ and $R^6$ are each independently a substituent group having up to 40 carbon atoms,
the process comprising the following steps:
(a) providing a compound of formula (IV):

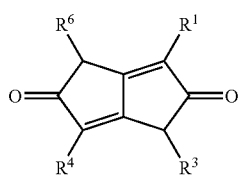

wherein $R^1$, $R^3$, $R^4$ and $R^6$ are each independently a substituent group having up to 40 carbon atoms;
(b) adding the compound of formula (IV) to a source of $R^2$ and $R^5$ at below 0° C. and allowing to react; and
(c) stopping the reaction to provide a compound of formula (Ic).

Preferred definitions for $R^1$, $R^2$, $R^3$, $R^4$, $R^5$ and $R^6$ are as given in relation to the third aspect.

Step (b) may use metal halides (e.g. Grignard reagents) or organolithium compounds as the source of $R^2$ and $R^5$. For example, metal halide compounds of formula $RMX_2$ (where R is $R^2$ or $R^5$, M is a metal and X is a halide) may be used. M may in particular be a transition metal, e.g. Mn, or a lanthanide, e.g. Ce.

In a preferred embodiment, step (b) uses cerium chloride compounds ($RCeCl_2$ where R is $R^2$ or $R^5$) as the source of $R^2$ and $R^5$.

In a preferred embodiment, $R^2$ and $R^5$ are the same and therefore only a single source of $R^2$ and $R^5$ is required.

Preferably, the reaction of step (b) is carried out in solution, for example in non-aqueous solution, such as in THF or ether.

The reaction in step (b) is suitably carried out at −10° C. or lower, for example −20° C. or lower, preferably −40° C. or lower, such as −60° C. or lower, e.g. −70° C. or lower.

Preferably, in step (b) the source of $R^2$ and $R^5$ is stirred. Preferably the compound of formula (IV) is added into the vortex of stirring, most preferably the compound of formula (IV) is added dropwise into the vortex of stirring.

In step (c) the reaction may be stopped by warming to 0° C. or higher, such as 5° C. or higher, for example to 10° C. or higher, such as to room temperature or higher. Alternatively, the reaction can be quenched at below 0° C., for example it may be quenched at −40° C. or lower, such as −60° C. or lower, e.g. −70° C. or lower.

Preferably the compound of formula (IV) is added to the source of $R^2$ and $R^5$ in a molar ratio of 1:4 to 1:2, more preferably about 1:3.

The compound of formula (IV) may have been obtained from a compound of formula (III) using step (c) described in the process of the eleventh aspect. In turn the compound of formula (III) may have been obtained from a compound of formula (II) using step (b) described in the process of the eleventh aspect. Further, the compound of formula (II) may have been obtained from a compound of formula (IIa) using step (a2) described in the process of the eleventh aspect.

Preferably, the reaction is performed under an inert atmosphere, for example under $N_2$, for the steps where organometallic reagents are used. Preferably, the reaction is performed with dry solvents for the steps where organometallic reagents are used.

The present invention also provides, in a thirteenth aspect, a process for the production of a substituted pentalene of formula (Ib):

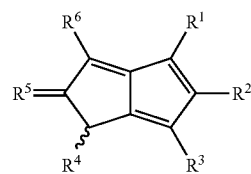

wherein $R^1$, $R^2$, $R^3$, $R^4$, $R^5$ and $R^6$ are each independently a substituent group having up to 40 carbon atoms;
the process comprising the steps of:
(a) providing a compound of formula (Ic):

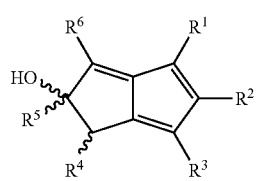

wherein $R^1$, $R^2$, $R^3$, $R^4$, $R^5$ and $R^6$ are each independently a substituent group having up to 40 carbon atoms wherein the $R^5$ group includes at least one H;
(b) dehydrating the compound of formula (Ic) to give a compound of formula (Ib).

Preferred definitions for $R^1$, $R^2$, $R^3$, $R^4$, $R^5$ and $R^6$ are as given in relation to the third aspect.

The compound of formula (Ic) may have been obtained by a process according to the twelfth aspect.

Preferably step (b) is carried out under aprotic conditions.

Preferably, the dehydration of step (b) is carried out using LiX or $MgX_2$, where X is selected from F, Cl, Br and I, and each X may be the same or different. Preferably, the dehydrating agent is selected from LiCl or $MgCl_2$. However, other dehydrating agents, in particular other dehydrating agents that do not involve acidic reagents or products, such as Burgess' reagent, may alternatively be used.

Step (b) may preferably be carried out in an aprotic solvent such as DMSO.

The invention further provides, in a fourteenth aspect, a process for the production of a substituted pentalene of formula (Ie):

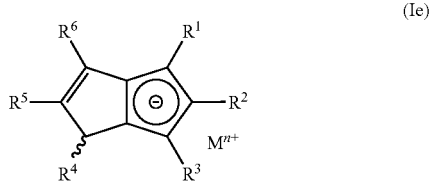

(Ie)

wherein R¹, R², R³, R⁴, R⁵ and R⁶ are each independently a substituent group having up to 40 carbon atoms, M is an alkali or alkaline earth metal and n represents the valency of the metal M;
the process comprising the steps of:
(a) providing a compound of formula (Ib):

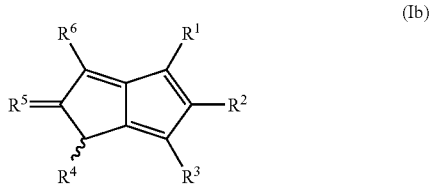

(Ib)

wherein R¹, R², R³, R⁴, R⁵ and R⁶ are each independently a substituent group having up to 40 carbon atoms;
(b) reacting the compound of formula (Ib) with a source of metal hydride.

Preferred definitions for R¹, R², R³, R⁴, R⁵ and le are as given in relation to the third aspect.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

The source of metal hydride may be any suitable source wherein the metal is the metal M. Preferably, the metal M is lithium, sodium or potassium and therefore the source of metal hydride is a source of lithium hydride, sodium hydride or potassium hydride respectively.

Preferably sterically bulky complexes are used as the source of metal hydride, such as metal trisiamylborohydrides, metal triethylborohydrides, metal tri-trans-2-methylcyclopentylborohydrides, metal dimesitylborohydrides, metal 2,6-di-tert-butylphenoxyneopentoxyaluminumhydrides, or metal tri-sec-butylborohydrides.

In one embodiment, the metal M is lithium and therefore the source of metal hydride is a source of lithium hydride. It may in particular be a lithium trialkylborohydride, such as lithium trisiamylborohydride (LS-Selectride) or lithium tri-sec-butylborohydride (L-Selectride).

Step (b) may be carried out in any suitable solvent system and under any suitable conditions. Preferably, step (b) is carried out in a non-aqueous, non-protic solvent such as Et₂O, THF or TMEDA. The reaction in step (b) may be continued for any suitable length of time, for example 12 hours or more, such as 24 hours or more, e.g. 48 hours or more.

The compound of formula (Ib) may have been obtained by a process in accordance with the thirteenth aspect.

Preferably, the process is carried out under an inert atmosphere, for example a N₂ atmosphere. Suitably, dry solvents are used.

The invention further provides, in a fifteenth aspect, a process for the production of a substituted pentalene of formula (If):

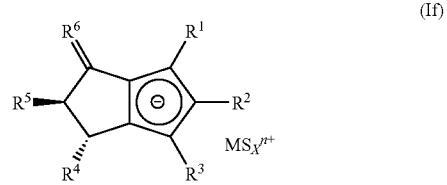

(If)

wherein R¹, R², R³, R⁴, R⁵ and R⁶ are each independently a substituent group having up to 40 carbon atoms, M is an alkali or alkaline earth metal and n represents the valency of the metal M, S is a chelating solvent and X is a number from 0 to 10;
the process comprising the steps of:
(a) providing a compound of formula (Ia):

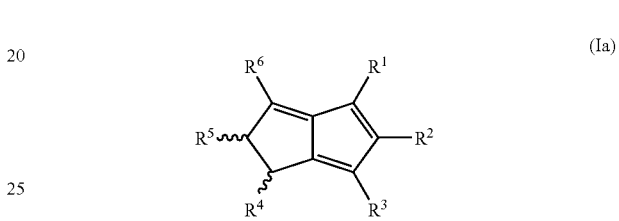

(Ia)

wherein R¹, R², R³, R⁴, R⁵ and R⁶ are each independently a substituent group having up to 40 carbon atoms;
(b) reacting the compound of formula (Ia) with a source of the metal M in the chelating solvent S.

Preferred definitions for R¹, R², R³, R⁴, R⁵ and R⁶ are as given in relation to the second aspect.

Preferred values for X are as in the seventh aspect above.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

S may be any chelating solvent. In one embodiment, S is dimethoxyethane (DME), N,N,N',N'-tetramethylethylenediamine (TMEDA) or tetrahydrofuran (THF). Preferably, S is DME.

In step (b) the source of metal may be provided in the chelating solvent alone, or additional solvent may also be present. In one embodiment, pentane is additionally present.

Preferably, the source of metal is an alkyl metal reagent (such as a C1-6, e.g. C1-4, alkyl metal reagent; for example an n-butyl metal reagent, s-butyl metal reagent or methyl metal reagent) or a metal amide. In a preferred embodiment, M may be lithium and the source of metal may be a lithium amide or an alkyl lithium reagent, such as n-butyl lithium, s-butyl lithium or methyl lithium. In another embodiment, M may be sodium and the source of metal may be a sodium amide or an alkyl sodium reagent. In another embodiment, M may be potassium and the source of metal may be a potassium amide or an alkyl potassium reagent.

Step (b) may preferably be carried out at low temperature, such as −10° C. or lower, for example −20° C. or lower, preferably −40° C. or lower, such as −60° C. or lower, e.g. −70° C. or lower.

The compound of formula (Ia) may have been obtained by a process in accordance with the eleventh aspect.

Preferably, the process is carried out under an inert atmosphere, for example a N₂ atmosphere. Suitably, dry solvents are used.

The invention further provides, in a sixteenth aspect, a process for the production of a substituted pentalene of formula (Ig):

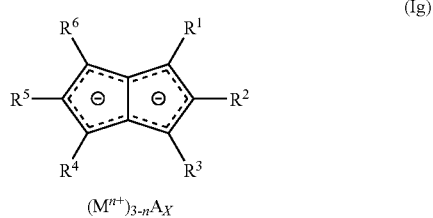

wherein $R^1$, $R^2$, $R^3$, $R^4$, $R^5$ and $R^6$ are each independently a substituent group having up to 40 carbon atoms, M is an alkali or alkaline earth metal and n represents the valency of the metal M, A is a tertiary amine and X is a number from 0 to 10; the process comprising the steps of:
(a) providing a compound of formula (Ie):

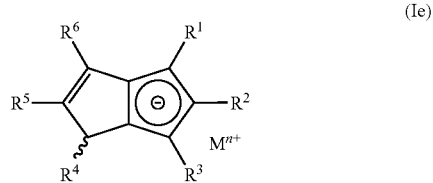

wherein $R^1$, $R^2$, $R^3$, $R^4$, $R^5$ and $R^6$ are each independently a substituent group having up to 40 carbon atoms, M is an alkali or alkaline earth metal and n represents the valency of the metal M; and
(b) reacting the compound of formula (Ie) with a source of metal M in the tertiary amine A.

Preferred definitions for $R^1$, $R^2$, $R^3$, $R^4$, $R^5$ and $R^6$ are as given in relation to the third aspect.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

A may be any tertiary amine. Preferably, A is a tertiary diamine. In one embodiment, A is tetraethylethylenediamine, tetramethylpropanediamine or tetramethylethanediamine. Preferably, A is N,N,N',N'-tetramethyl-ethane-1,2-diamine (TMEDA).

In step (b) the source of metal may be provided in the tertiary amine A alone, or, preferably, additional solvent may also be present. In one embodiment, a non-polar solvent, e.g. hexane or benzene, is additionally present.

The source of metal M may be any suitable source. Preferably, the source of metal is an alkyl metal reagent (such as a C1-6, e.g. C1-4, alkyl metal reagent; for example an n-butyl, s-butyl or methyl metal reagent) or a metal amide. For example, when the metal M is lithium, the source of metal may be an alkyl lithium reagent such as n-butyl lithium, s-butyl lithium or methyl lithium.

Step (b) may preferably be carried out at reflux. The reaction in step (b) may be continued for any suitable length of time, for example 24 hours or more, such as 48 hours or more, e.g. 72 hours or more.

The compound of formula (Ie) may be provided in step (a) in a solvent, in particular a non-aqueous solvent, such as hexane.

Preferably, X is from 0.05 to 0.6, more preferably from 0.1 to 0.5, such as from 0.1 to 0.4, e.g. from 0.15 to 0.3, most preferably from 0.15 to 0.25.

The compound of formula (Ie) may have been obtained by the process of the fourteenth aspect.

Preferably, the process is carried out under an inert atmosphere, for example a $N_2$ atmosphere. Suitably, dry solvents are used.

The invention further provides, in a seventeenth aspect, a process for the production of a substituted pentalene of formula (Id):

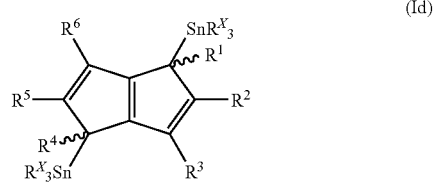

wherein $R^x$, $R^1$, $R^2$, $R^3$, $R^4$, $R^5$ and $R^6$ are each independently a substituent group having up to 40 carbon atoms;
the process comprising the steps of:
(a) providing a substituted pentalene of formula (Ig):

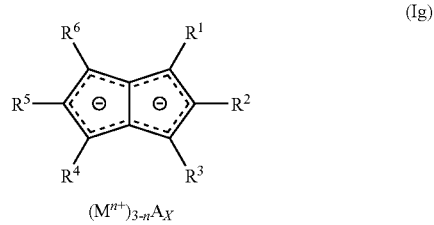

wherein $R^1$, $R^2$, $R^3$, $R^4$, $R^5$ and $R^6$ are each independently a substituent group having up to 40 carbon atoms, M is an alkali or alkaline earth metal and n represents the valency of M, A is a tertiary amine and X is a number from 0 to 10;
(b) reacting the compound of formula (Ig) with a source of $SnR^x_3$, where $R^x$ is a substituent group having up to 40 carbon atoms.

Preferred definitions for $R^1$, $R^2$, $R^3$, $R^4$, $R^5$ and $R^6$ are as given in relation to the third aspect.

Preferably each $R^x$ is the same. For example, each $R^x$ may be a branched or unbranched C1-12 alkyl group (more preferably branched or unbranched C1-8 alkyl, e.g. C1-6 branched or unbranched alkyl, most preferably C1, 2, 3 or 4 unbranched alkyl), or a C1-4 alkoxy group.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

A may be any tertiary amine. Preferably, A is a tertiary diamine. In one embodiment, A is tetraethylethylenediamine, tetramethylpropanediamine or tetramethylethanediamine. Preferably, A is N,N,N',N'-tetramethyl-ethane-1,2-diamine (TMEDA).

Preferably, X is from 0.05 to 0.6, e.g. from 0.1 to 0.5, such as from 0.1 to 0.4, e.g. from 0.15 to 0.3, most preferably from 0.15 to 0.25.

The source of $SnR^x_3$ may be any suitable source; preferably it is a halide salt of $SnR^x_3$, for example the chloride or bromide salt of $SnR^x_3$.

The compound of formula (Ig) may have been obtained by a process in accordance with the sixteenth aspect.

Preferably, the process is carried out under an inert atmosphere, for example a $N_2$ atmosphere. Suitably, dry solvents are used.

The invention further provides, in an eighteenth aspect, a process for the production of a substituted pentalene of formula (Ig):

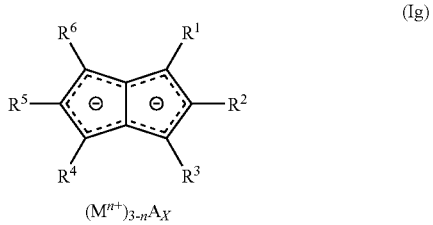

wherein $R^1$, $R^2$, $R^3$, $R^4$, $R^5$ and $R^6$ are each independently a substituent group having up to 40 carbon atoms, M is an alkali or alkaline earth metal and n represents the valency of M, A is a tertiary amine and X is a number from 0 to 10;
the process comprising the steps of:
(a) providing a compound of formula (Id):

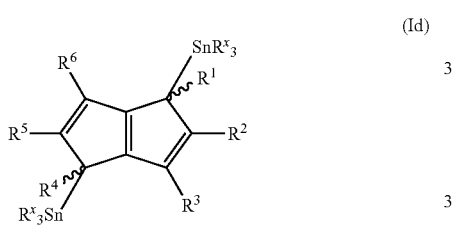

wherein $R^x$, $R^1$, $R^2$, $R^3$, $R^4$, $R^5$ and $R^6$ are each independently a substituent group having up to 40 carbon atoms;
(b) reacting the compound of formula (Id) with a source of metal M in the presence of the tertiary amine A.

Preferred definitions for $R^1$, $R^2$, $R^3$, $R^4$, $R^5$ and $R^6$ are as given in relation to the third aspect.

Preferably each $R^x$ is the same. For example, each $R^x$ may be a branched or unbranched C1-12 alkyl group (more preferably branched or unbranched C1-8 alkyl, e.g. C1-6 branched or unbranched alkyl, most preferably C1, 2, 3 or 4 unbranched alkyl), or a C1-4 alkoxy group.

In a preferred embodiment, M is an alkali metal. Accordingly, n is 1. M may, for example, be Li, Na or K.

In an alternative embodiment, M is an alkaline earth metal. Accordingly, n is 2. M may, for example, be Mg or Ca.

A may be any tertiary amine. Preferably, A is a tertiary diamine. In one embodiment, A is tetraethylethylenediamine, tetramethylpropanediamine or tetramethylethanediamine. Preferably, A is N,N,N',N'-tetramethyl-ethane-1,2-diamine (TMEDA). The amine A may be provided in a solvent, particularly a non-polar solvent e.g. hexane or benzene.

The source of metal M may be any suitable source, for example an alkyl metal reagent (such as a C1-6, e.g. C1-4, alkyl metal reagent; for example an n-butyl metal reagent, s-butyl metal reagent or methyl metal reagent) or a metal amide. The source of metal M may be an alkyl silyl metal reagent such as $Me_3SiCH_2M$.

In one embodiment, M is lithium and the source of lithium is an alkyl lithium such as n-butyl lithium, s-butyl lithium or methyl lithium.

In one embodiment, M is sodium or potassium and the source of sodium or potassium is an alkyl silyl sodium reagent or alkyl silyl potassium reagent respectively, such as $Me_3SiCH_2M$ (where M=Na or K).

Step (b) may preferably be carried out at room temperature.

In one embodiment, the tertiary amine A is present due to the compound of formula (Id) being provided in step (a) in the tertiary amine A. Alternatively, or additionally, the tertiary amine A may be added in step (b).

The source of metal M may be provided in a solvent, preferably a non-aqueous solvent. When the metal M is lithium, the solvent is preferably a non-aqueous, non-protic solvent such as Et2O, THF or TMEDA. When the metal M is sodium or potassium, the solvent is preferably a non-aqueous, non-polar solvent e.g. hexane or benzene.

Preferably, X is from 0 to 2, e.g. from 1 to 2, more preferably from 1.5 to 2, most preferably X is about 2.

The compound of formula (Id) may have been obtained by the process of the seventeenth aspect.

Preferably, the process is carried out under an inert atmosphere, for example a $N_2$ atmosphere. Suitably, dry solvents are used.

The invention also provides, in a nineteenth aspect, a process for preparing a substituted pentalene of formula (I):

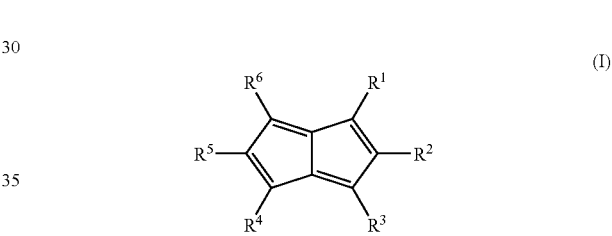

wherein $R^1$, $R^2$, $R^3$, $R^4$, $R^5$ and $R^6$ are each independently a substituent group having up to 40 carbon atoms;
the process comprising the steps of:
(a) providing a compound of formula (X):

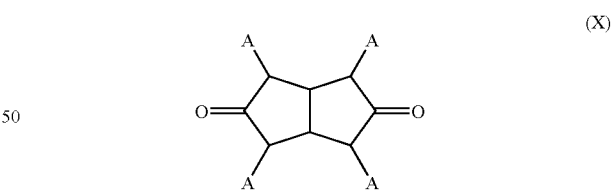

wherein A is a carboxylate group;
(b) reacting the compound of formula (X) with acid to obtain a compound of formula (XI):

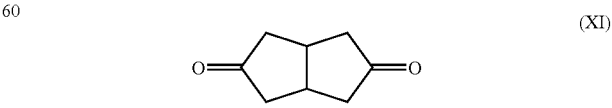

(c) reacting the compound of formula (XI) with a source of Y to obtain a compound of formula (XII):

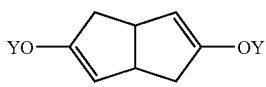

(XII)

wherein OY is a protecting/activating group;
(d) reacting the compound of formula (XII) with a source of R$^1$ and R$^4$ to obtain a compound of formula (XIII):

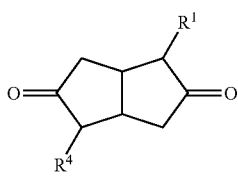

(XIII)

(e) reacting the compound of formula (XIII) with a source of Y to obtain a compound of formula (XIV):

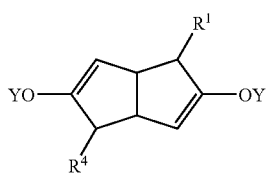

(XIV)

wherein OY is a protecting/activating group;
(f) reacting the compound of formula (XIV) with a source of R$^3$ and R$^6$ to obtain a compound of formula (XV):

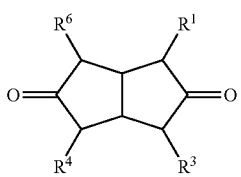

(XV)

(g) oxidising the compound of formula (XV) to produce a compound of formula (XVI)

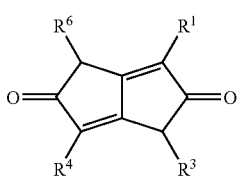

(XVI)

(h) reacting the compound of formula (XVI) with a source of R$^2$ and R$^5$, followed by dehydration with a dehydrating agent, to obtain a compound of formula (I).

Each of R$^1$, R$^2$, R$^3$, R$^4$, R$^5$ and R$^6$ may be any substituent group (i.e. a group that substitutes a hydrogen group on a carbon atom), provided that it has no more than 40 carbon atoms. Preferred definitions of these groups are as in relation to the first aspect above.

In one embodiment, R$^1$, R$^2$, R$^3$, R$^4$, R$^5$ and R$^6$ are the same. In one particular embodiment, R$^1$, R$^2$, R$^3$, R$^4$, R$^5$ and R$^6$ are the same and are branched C4-12 alkyl groups, e.g. branched C4-8 alkyl groups, such as s-butyl or t-butyl.

In one embodiment, R$^1$, R$^2$, R$^3$, R$^4$, R$^5$ and R$^6$ are not all the same. For example, R$^1$ and R$^4$ may be the same as each other, but differ from the remaining R groups. R$^3$ and R$^6$ may be the same as each other, but differ from the remaining R groups. R$^2$ and R$^5$ may be the same as each other, but differ from the remaining R groups.

Preferably, A is a carboxylate group COOR', where R' is hydrogen or C1-8 branched or unbranched alkyl, for example R' may be hydrogen or C1-4 alkyl, such as methyl, ethyl or n-propyl.

In step (b), the acid may be any suitable acid provided that it is non-oxidising towards the compound of formula (X). Preferably, the acid is a non-oxidant. Preferably, the acid is a strong acid, for example an acid with a pKa (as measured at 25° C.) of 3 or lower, such as 2 or lower, preferably 1 or lower, for example from −6 to 0. Examples of acids that can be used include inorganic acids such as HX, where X=Cl, Br or I, and organic acids such as triflic acid or trifluoracetic acid. Preferably, the acid is hydrochloric acid.

In steps (c) and (e) the protecting/activating group OY may be any suitable ester protecting group. In one embodiment, the protecting/activating group OY is a silyl ester protecting group, for example the protecting/activating group OY may be OSiR$_3$ where R is branched or unbranched C1-8 alkyl, preferably branched or unbranched C1-4 alkyl, e.g. methyl, ethyl or iso-propyl. In one embodiment, the protecting/activating group OY is a trimethylsilyl ester protecting group.

In an alternative embodiment, Y may be a metal, preferably an alkali or alkaline earth metal; for example Y may be Li, Na or K.

The source of group Y may be chosen appropriately in view of the nature of the protecting group OY. In one embodiment, a halide source of the group Y may be used, such as a chloride source. For example, if the protecting group is a silyl ester protecting group, a silyl halide may be used to provide the protecting group. Equally, if Y is a metal then a metal halide may be used as the source.

Steps (c) and (e) may be carried out in a suitable solvent, for example a non-aqueous solvent such as DMF or THF.

Steps (c) and (e) may preferably be carried out under basic conditions. In particular, an amine, such as lithium diisopropylamide (LDA), trimethylamine or triethylamine, may be present. In one embodiment, step (c) is carried out in the presence of triethylamine. In one embodiment, step (e) is carried out in the presence of LDA. In this embodiment, Y may in particular be Li or Na, or may be a silyl group.

One or both of the steps (c) and (e) may be carried out at low temperature, for example −10° C. or lower, such as −20° C. or lower, preferably −40° C. or lower, such as −60° C. or lower, e.g. −70° C. or lower.

In one embodiment, step (c) may be carried out using trimethylsilyl chloride with triethylamine and DMF to provide trimethylsilyl ester protecting groups. The step may be carried out in accordance with *Pure Appl. Chem.* 43 (1975) p553; H. O. House: *Modern Synthetic Reactions, 2$^{nd}$ Ed.*, W. A. Benjamin, Menlo Park, 1972; and D. Caine in R. L. Augustine: *Carbon-Carbon bond formation*, Vol 1, Marcel Dekker, New York, 1979.

In one embodiment, step (e) may be carried out using trimethylsilyl chloride with LDA and THF to provide trimethylsilyl ester protecting groups. The step may be carried out in accordance with *Pure Appl. Chem.* 43 (1975) p553; H. O. House: *Modern Synthetic Reactions, 2$^{nd}$ Ed.*, W. A. Benjamin, Menlo Park, 1972; or D. Caine in R. L. Augustine: *Carbon-Carbon bond formation*, Vol 1, Marcel Dekker, New York, 1979.

In steps (d), (f) and (h), the sources of $R^1$, $R^2$, $R^3$, $R^4$, $R^5$ and $R^6$ may be any suitable source. The source of each of $R^1$, $R^2$, $R^3$, $R^4$, $R^5$ and $R^6$ may generally be represented as RY', where R is $R^1$, $R^2$, $R^3$, $R^4$, $R^5$ and $R^6$ and Y' is a leaving group. RY' may contain a pendant heteroatom donor (e.g. $ICH_2CH_2CH_2L$ where L is NR2, $PR_2$, OR or SR). The sources of each of $R^1$, $R^2$, $R^3$, $R^4$, $R^5$ and $R^6$ may have the same leaving group Y' or may have different leaving groups Y'.

The source of some or all of $R^1$, $R^2$, $R^3$, $R^4$, $R^5$ and $R^6$ may be a halide salt thereof, such as the chlorine, bromine or iodine salt thereof.

When a source of R in any of steps (d), (f) and (h) is a halide salt thereof, a Lewis acid may suitably also be present. Examples of Lewis acids include aluminium chloride, iron (III) chloride, boron trifluoride, titanium (IV) chloride, niobium pentachloride and ytterbium(III) triflate. Preferably, the Lewis acid used is titanium (IV) chloride, aluminium chloride or boron trifluoride.

A suitable solvent may also be used. In particular a non-aqueous solvent, such as tetrahydrofuran, dichloromethane or trichloromethane, may be used.

When a source of R in any of steps (d), (f) and (h) is a halide salt thereof, the step may be carried out in accordance with *Chemische Berichte* (1980), 113(12), 3741-57; *Angew. Chem. Intl. Ed. Engl.*, 21, (1982) p 96-108; or *Angew. Chem. Intl. Ed. Engl.*, 17 (1978) p 48.

The source of some or all of $R^1$, $R^2$, $R^3$, $R^4$, $R^5$ and $R^6$ may be a metal halide compound ($RMX_2$ where R is $R^1$, $R^2$, $R^3$, $R^4$, $R^5$ or $R^6$, M is a metal and X is a halide). The metal M may in particular be a transition metal, e.g. Mn, or a lanthanide, e.g. Ce. Cerium chloride compounds ($RCeCl_2$) are particularly preferred.

Metal halide compounds $RMX_2$ (where R is $R^1$, $R^2$, $R^3$, $R^4$, $R^5$ or $R^6$, M is a metal and X is a halide) may be provided by the use of RM' (where M' is Li, Na or K) plus $MX_3$.

A solvent, example a non-aqueous solvent such as tetrahydrofuran, dichloromethane or trichloromethane, may be used. When the source of R is the cerium chloride compound $RCeCl_2$, the preferred solvent is tetrahydrofuran.

In one embodiment, in steps (d) and (f), the source of R is a halide salt thereof, such as the chloride salt thereof. In particular, the source of R may be provided in the presence of a Lewis acid, such as titanium (IV) chloride. Dichloromethane may be used as solvent.

In one embodiment, in step (h) the source of R is a metal halide compound, such as the cerium chloride compound $RCeCl_2$. THF may be used as the solvent.

In a preferred embodiment, $R^1$, $R^2$, $R^3$, $R^4$, $R^5$ and $R^6$ are the same and therefore in each step only a single source is required.

In step (g), the oxidising agent may be any suitable agent. The oxidising agent may, preferably, be selected from chlorine, bromine, potassium permanganate, or potassium dichromate. In one embodiment, the oxidising agent is bromine.

In step (h) the dehydrating agent is preferably LiX or $MgX_2$, where X is selected from F, Cl, Br and I, and each X may be the same or different. More preferably, the dehydrating agent is selected from LiCl or $MgCl_2$. However, other dehydrating agents, in particular other dehydrating agents that do not involve acidic reagents or products, such as Burgess' reagent, may alternatively be used.

The dehydration of step (h) may preferably be carried out in an aprotic solvent such as DMSO. The use of DMSO is particularly preferred when the source of R in step (h) is the cerium chloride compound $RCeCl_2$.

The invention also provides, in a twentieth aspect, a process for preparing a substituted pentalene of formula (I):

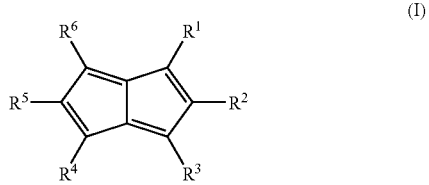

(I)

wherein IV, $R^2$, $R^3$, $R^4$, $R^5$ and $R^6$ are each independently a substituent group having up to 40 carbon atoms;
the process comprising the steps of:
(a) providing a compound of formula (X):

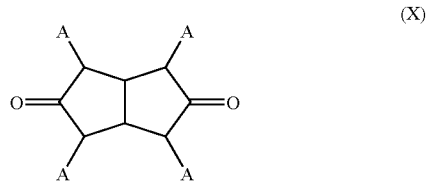

(X)

wherein A is a carboxylate group;
(b) reacting the compound of formula (X) with a source of $R^1$, followed by decarboxylation, to obtain a compound of formula (XX):

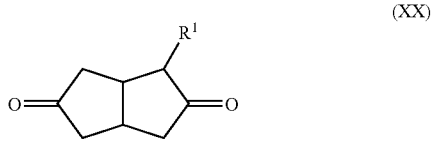

(XX)

(c) mono-ketalising the compound of formula (XX) to obtain a compound of formula (XXI):

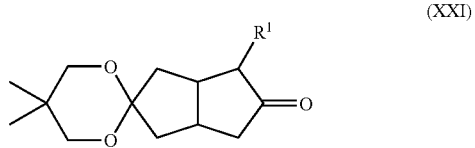

(XXI)

(d) carrying out an enolisation and electrophilic trapping reaction on the compound of formula (XXI) with a source of $R^3$ to obtain a compound of formula (XXII):

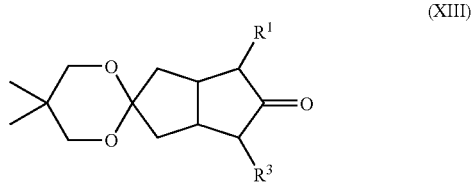

(XIII)

(e) deketalising the compound of formula (XXIII), followed by reaction with a source of $R^4$ and $R^6$ to obtain a compound of formula (XV):

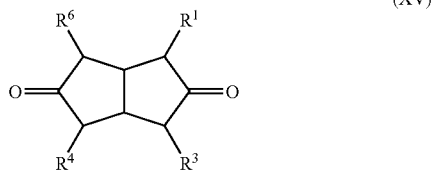

(XV)

(f) oxidising the compound of formula (XV) to produce a compound of formula (XVI)

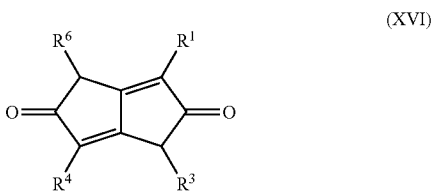

(XVI)

(g) reacting the compound of formula (XVI) with a source of $R^2$ and $R^5$, followed by dehydration with a dehydrating agent, to obtain a compound of formula (I).

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the first aspect above.

In one embodiment, each of $R^1$, $R^2$, $R^3$, $R^4$, $R^5$ and $R^6$ is different.

In one embodiment, at least $R^1$ and $R^3$ are different. $R^1$ may be the same as the remaining R groups, or may be different to some or all of the remaining R groups. $R^3$ may be the same as the remaining R groups, or may be different to some or all of the remaining R groups.

In one embodiment, at least $R^4$ and $R^6$ are different. $R^4$ may be the same as the remaining R groups, or may be different to some or all of the remaining R groups. $R^6$ may be the same as the remaining R groups, or may be different to some or all of the remaining R groups.

In one embodiment, $R^2$ and $R^5$ are the same. $R^2$ and $R^5$ preferably differ from some or all of the remaining R groups.

Preferably, A is a carboxylate group COOR', where R' is hydrogen or C1-8 branched or unbranched alkyl, for example R' may be hydrogen or C1-4 alkyl, such as methyl, ethyl or n-propyl.

In steps (b), (e) and (g), the sources of $R^1$, $R^2$, $R^3$, $R^4$, $R^5$ and $R^6$ may be any suitable source. The source of each of $R^1$, $R^2$, $R^3$, $R^4$, $R^5$ and $R^6$ may generally be represented as RY', where R is $R^1$, $R^2$, $R^3$, $R^4$, $R^5$ and $R^6$ and Y' is a leaving group. RY' may contain a pendant heteroatom donor (e.g. $ICH_2CH_2CH_2L$ where L is NR2, $PR_2$, OR or SR). The sources of each of $R^1$, $R^2$, $R^3$, $R^4$, $R^5$ and $R^6$ may have the same leaving group Y' or may have different leaving groups Y'.

The source of some or all of $R^1$, $R^2$, $R^3$, $R^4$, $R^5$ and $R^6$ may be a halide salt thereof, such as the chlorine, bromine or iodine salt thereof.

The source of some or all of $R^1$, $R^2$, $R^3$, $R^4$, $R^5$ and $R^6$ may be a metal halide compound ($RMX_2$ where R is $R^1$, $R^2$, $R^3$, $R^4$, $R^5$ or $R^6$, M is a metal and X is a halide). M may be a transition metal, e.g. Mn, or a lanthanide, e.g. Ce. Cerium chloride compounds ($RCeCl_2$) are particularly preferred.

Steps (b), (e) and (g) may be carried out using a solvent, in particular a non-aqueous solvent, such as DMF, dichloromethane or trichloromethane.

Steps (b) and (e) may preferably be carried out under basic conditions. In particular, a base such as potassium hydride or an amine, e.g. lithium diisopropylamide (LDA), trimethylamine or triethylamine, may be present. In one embodiment, step (b) is carried out in the presence of potassium hydride, whilst step (e) is carried out in the presence of LDA.

In step (b), the decarboxylation may be carried out using known decarboxylation techniques.

In step (c), the ketalisation may be carried out using known ketalisation agents and techniques; whilst in step (e) the ketalising agent may be removed using known deketalisation techniques.

In step (f), the oxidising agent may be any suitable agent. The oxidising agent may, preferably, be selected from chlorine, bromine, potassium permanganate, or potassium dichromate. In one embodiment, the oxidising agent is bromine.

In step (g) the dehydrating agent is preferably LiX or $MgX_2$, where X is selected from F, Cl, Br and I, and each X may be the same or different. More preferably, the dehydrating agent is selected from LiCl or $MgCl_2$. However, other dehydrating agents, in particular other dehydrating agents that do not involve acidic reagents or products, such as Burgess' reagent, may alternatively be used.

The dehydration of step (g) may preferably be carried out in an aprotic solvent such as DMSO.

The present invention also provides, in a twenty-first aspect, a process for preparing a substituted pentalene of formula (I):

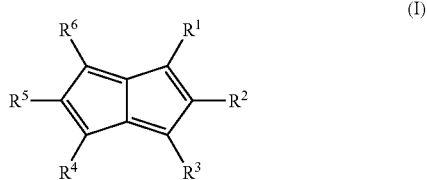

(I)

wherein $R^1$, $R^2$, $R^3$, $R^4$, $R^5$ and $R^6$ are each independently a substituent group having up to 40 carbon atoms;

the process comprising the steps of:

(a) providing a compound of formula (XXV):

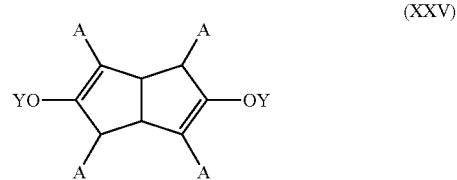

(XXV)

wherein A is a carboxylate group and Y is an alkali or alkaline earth metal;

(b) reacting the compound of formula (XXV) with a source of $R^3$ and $R^6$ to obtain a compound of formula (XXVI):

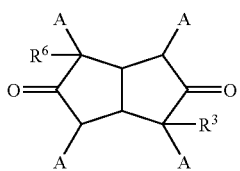

(XXVI)

(c) reacting the compound of formula (XXVI) with a source of Y to obtain a compound of formula (XXVII):

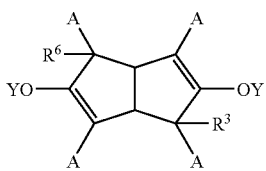

(XXVII)

wherein Y is an alkali or alkaline earth metal;
(d) reacting the compound of formula (XXVII) with a source of $R^1$ and $R^4$ to obtain a compound of formula (XXVIII):

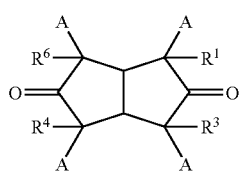

(XXVIII)

(e) decarboxylating the compound of formula (XXVIII), to obtain a compound of formula (XV):

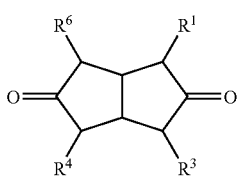

(XV)

(f) oxidising the compound of formula (XV) to produce a compound of formula (XVI)

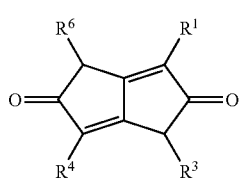

(XVI)

(g) reacting the compound of formula (XVI) with a source of $R^2$ and $R^5$, followed by dehydration with a dehydrating agent, to obtain a compound of formula (I).

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the first aspect above.

Preferably, $R^3$ and $R^6$ are the same. The remaining R groups may be the same as $R^3$ and $R^6$, or may be different to $R^3$ and $R^6$. For example, $R^1$ and $R^4$ may be the same as $R^3$ and $R^6$, and/or $R^2$ and $R^5$ may be the same as $R^3$ and $R^6$.

Preferably, $R^1$ and $R^4$ are the same. The remaining R groups may be the same as $R^1$ and $R^4$, or may be different to $R^1$ and $R^4$. For example, $R^3$ and $R^6$ may be the same as $R^1$ and $R^4$, and/or $R^2$ and $R^5$ may be the same as $R^1$ and $R^4$.

Preferably, $R^2$ and $R^5$ are the same. The remaining R groups may be the same as $R^2$ and $R^5$, or may be different to $R^2$ and $R^5$. For example, $R^3$ and $R^6$ may be the same as $R^2$ and $R^5$, and/or $R^1$ and $R^4$ may be the same as $R^2$ and $R^5$.

Preferably, A is a carboxylate group COOR', where R' is hydrogen or C1-8 branched or unbranched alkyl, for example R' may be hydrogen or C1-4 alkyl, such as methyl, ethyl or n-propyl.

Preferably, Y is lithium, sodium or potassium. In step (c), the source of Y may be YOR', where R' is C1-4 alkyl, e.g. methyl or ethyl. For example, the source of Y may be YOMe. Step (c) may be carried out in a solvent, preferably a non-aqueous solvent, such as methanol or ethanol, or DMSO.

In steps (b), (d) and (g), the sources of $R^1$, $R^2$, $R^3$, $R^4$, $R^5$ and $R^6$ may be any suitable source. The source of each of $R^1$, $R^2$, $R^3$, $R^4$, $R^5$ and $R^6$ may generally be represented as RY', where R is $R^1$, $R^2$, $R^3$, $R^4$, $R^5$ and $R^6$ and Y' is a leaving group. RY' may contain a pendant heteroatom donor (e.g. $ICH_2CH_2CH_2L$ where L is NR2, $PR_2$, OR or SR). The sources of each of $R^1$, $R^2$, $R^3$, $R^4$, $R^5$ and $R^6$ may have the same leaving group Y' or may have different leaving groups Y'.

The source of some or all of $R^1$, $R^2$, $R^3$, $R^4$, $R^5$ and $R^6$ may be a halide salt thereof, such as the chlorine, bromine or iodine salt thereof.

When a source of R in any of steps (b), (d) and (g) is a halide salt thereof, a Lewis acid may suitably also be present. Examples of Lewis acids include aluminium chloride, iron (III) chloride, boron trifluoride, titanium (IV) chloride, niobium pentachloride and ytterbium(III) triflate. Preferably, the Lewis acid used is titanium (IV) chloride, aluminium chloride or boron trifluoride.

A suitable solvent may also be used. In particular a non-aqueous solvent, such as tetrahydrofuran, dichloromethane or trichloromethane, may be used.

When a source of R in any of steps (b), (d) and (g) is a halide salt thereof, the step may be carried out in accordance with *Chemische Berichte* (1980), 113(12), 3741-57; *Angew. Chem. Intl. Ed. Engl.*, 21, (1982) p 96-108; or *Angew. Chem. Intl. Ed. Engl.*, 17 (1978) p 48.

The source of some or all of $R^1$, $R^2$, $R^3$, $R^4$, $R^5$ and $R^6$ may be a metal halide compound ($RMX_2$ where R is $R^1$, $R^2$, $R^3$, $R^4$, $R^5$ or $R^6$, M is a metal and X is a halide). The metal M may in particular be a transition metal, e.g. Mn, or a lanthanide, e.g. Ce. Cerium chloride compounds ($RCeCl_2$) are particularly preferred.

Metal halide compounds $RMX_2$ (where R is $R^1$, $R^2$, $R^3$, $R^4$, $R^5$ or $R^6$, M is a metal and X is a halide) may be provided by the use of RM' (where M' is Li, Na or K) plus $MX_3$.

A solvent, example a non-aqueous solvent such as tetrahydrofuran, dichloromethane or trichloromethane, may be used. When the source of R is the cerium chloride compound $RCeCl_2$, the preferred solvent is tetrahydrofuran.

In one embodiment, in steps (b) and (d), the source of R is a halide salt thereof, such as the chloride salt thereof. In particular, the source of R may be provided in the presence of a Lewis acid, such as titanium (IV) chloride. Dichloromethane may be used as solvent.

In one embodiment, in step (g) the source of R is a metal halide compound, such as the cerium chloride compound $RCeCl_2$. THF may be used as the solvent.

In step (e), the decarboxylation may be carried out using known decarboxylation techniques.

In step (f), the oxidising agent may be any suitable agent. The oxidising agent may, preferably, be selected from chlorine, bromine, potassium permanganate, or potassium dichromate. In one embodiment, the oxidising agent is bromine.

In step (g) the dehydrating agent is preferably LiX or $MgX_2$, where X is selected from F, Cl, Br and I, and each X may be the same or different. More preferably, the dehydrating agent is selected from LiCl or $MgCl_2$. However, other dehydrating agents, in particular other dehydrating agents that do not involve acidic reagents or products, such as Burgess' reagent, may alternatively be used.

The dehydration of step (g) may preferably be carried out in an aprotic solvent such as DMSO.

The present invention also provides, in a twenty-second aspect, a process for preparing a substituted pentalene of formula (I):

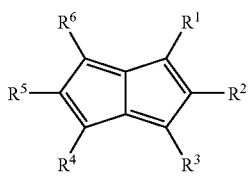

wherein $R^1$, $R^2$, $R^3$, $R^4$, $R^5$ and $R^6$ are each independently a substituent group having up to 40 carbon atoms;
the process comprising the steps of:
(a) providing a compound of formula (X):

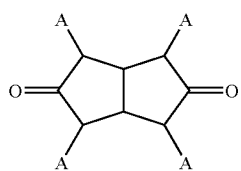

wherein A is a carboxylate group;
(b) reacting the compound of formula (X) with a source of $R^1$, $R^3$, $R^4$ and $R^6$ in the presence of a Lewis acid to obtain a compound of formula (II):

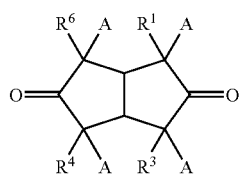

wherein $R^1$, $R^3$, $R^4$ and $R^6$ are each independently a substituent group having up to 40 carbon atoms and A is a carboxylate group;
(c) decarboxylating the compound of formula (II) to obtain a compound of formula (XV):

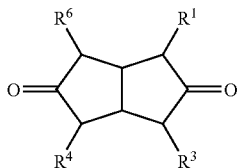

(d) oxidising the compound of formula (XV) to produce a compound of formula (XVI)

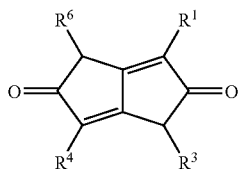

(e) reacting the compound of formula (XVI) with a source of $R^2$ and $R^5$, followed by dehydration with a dehydrating agent, to obtain a compound of formula (I).

Each of $R^1$, $R^2$, $R^3$, $R^4$, $R^5$ and $R^6$ may be any substituent group (i.e. a group that substitutes a hydrogen group on a carbon atom), provided that it has no more than 40 carbon atoms. Preferred definitions of these groups are as in relation to the first aspect above.

Preferably, $R^1$, $R^2$, $R^3$, $R^4$, $R^5$ and $R^6$ are the same.

In one embodiment, $R^1$, $R^2$, $R^3$, $R^4$, $R^5$ and $R^6$ are the same and are branched C4-12 alkyl groups, e.g. branched C4-8 alkyl groups, such as s-butyl or t-butyl.

Preferably, A is a carboxylate group COOR', where R' is hydrogen or C1-8 branched or unbranched alkyl, for example R' may be hydrogen or C1-4 alkyl, such as methyl, ethyl or n-propyl.

In step (b), the Lewis acid may be any suitable acid. Examples of Lewis acids include aluminium chloride, iron (III) chloride, boron trifluoride, titanium (IV) chloride, niobium pentachloride and ytterbium(III) triflate. Preferably, the Lewis acid used in step (b) is aluminium chloride or boron trifluoride.

In steps (b) and (e), the sources of $R^1$, $R^2$, $R^3$, $R^4$, $R^5$ and $R^6$ may be any suitable source. The source of each of $R^1$, $R^2$, $R^3$, $R^4$, $R^5$ and $R^6$ may generally be represented as RY', where R is $R^1$, $R^2$, $R^3$, $R^4$, $R^5$ and $R^6$ and Y' is a leaving group. RY' may contain a pendant heteroatom donor (e.g. $ICH_2CH_2CH_2L$ where L is NR2, $PR_2$, OR or SR). The sources of each of $R^1$, $R^2$, $R^3$, $R^4$, $R^5$ and $R^6$ may have the same leaving group Y' or may have different leaving groups Y'.

The source of some or all of $R^1$, $R^2$, $R^3$, $R^4$, $R^5$ and $R^6$ may be a halide salt thereof, such as the chlorine, bromine or iodine salt thereof.

The source of some or all of $R^1$, $R^2$, $R^3$, $R^4$, $R^5$ and $R^6$ may be a metal halide compound ($RMX_2$ where R is $R^1$, $R^2$, $R^3$, $R^4$, $R^5$ or $R^6$, M is a metal and X is a halide). The metal M may in particular be a transition metal, e.g. Mn, or a lanthanide, e.g. Ce. Cerium chloride compounds ($RCeCl_2$) are particularly preferred.

Metal halide compounds $RMX_2$ (where R is $R^1$, $R^2$, $R^3$, $R^4$, $R^5$ or $R^6$, M is a metal and X is a halide) may be provided by the use of RM' (where M' is Li, Na or K) plus $MX_3$. A solvent, for example a non-aqueous solvent such as tetrahydrofuran, dichloromethane or trichloromethane, may be used. When the source of R is the cerium chloride compound $RCeCl_2$, the preferred solvent is tetrahydrofuran.

In one embodiment, in step (b), the source of R is a halide salt thereof, such as the chloride salt thereof. In a preferred embodiment, $R^1$, $R^3$, $R^4$, and $R^6$ are the same and therefore only a single source is required.

Step (b) may be carried out using a solvent, in particular a non-aqueous solvent, for example a non-aqueous polar solvent such as nitromethane ($MeNO_2$).

Step (b) may be carried out using the methodology described in *Justus Liebigs der Annalen Chemie,* 718, p 101 (1968).

In one embodiment, in step (e) the source of R is a metal halide compound, such as the cerium chloride compound $RCeCl_2$. THF may be used as the solvent. In a preferred embodiment, $R^2$ and $R^5$ are the same and therefore only a single source is required.

In step (c), the decarboxylation may be carried out using known decarboxylation techniques.

In step (d), the oxidising agent may be any suitable agent. The oxidising agent may, preferably, be selected from chlorine, bromine, potassium permanganate, or potassium dichromate. In one embodiment, the oxidising agent is bromine.

In step (e) the dehydrating agent is preferably LiX or $MgX_2$, where X is selected from F, Cl, Br and I, and each X may be the same or different. More preferably, the dehydrating agent is selected from LiCl or $MgCl_2$. However, other dehydrating agents, in particular other dehydrating agents that do not involve acidic reagents or products, such as Burgess' reagent, may alternatively be used.

The dehydration of step (e) may preferably be carried out in an aprotic solvent such as DMSO. The use of DMSO is particularly preferred when the source of R in step (e) is the cerium chloride compound $RCeCl_2$.

The present invention also provides, in a twenty-third aspect, a process for the production of a complex in accordance with the ninth aspect, the process comprising reacting one or more ligand molecules of formula (I), (Ia), (Ib), (Ic), (Id), (Ie), (If), or (Ig) as defined above with a source of the metal.

Any suitable source of the metal may be used. In one embodiment, a metal carbonyl is used as the source of the metal. In an alternative embodiment, a metal halide may be used as this source of the metal.

In one embodiment, the ligand molecule may be of formula (Ib). In this embodiment, a metal carbonyl may suitably be used as the source of the metal. The metal may suitably be Fe, Ru, Co, Rh, Ir, Ni, Pd or Pt; for example Fe or Co. The process may, in this embodiment, suitably be carried out under reflux.

In another embodiment, the ligand molecule may be of formula (Ig). In this embodiment, a metal halide may suitably be used as the metal source. The metal may suitably be Sc, Y, Ti, Zr, Hf, V, La, Ce, Pr, Nd or Lu; for example, Ti, Zr or Ce. The process may, in this embodiment, suitably be carried out at 0° C. or lower, such as −20° C. or lower, preferably −40° C. or lower, such as −60° C. or lower, e.g. −70° C. or lower.

In a further embodiment, the ligand molecule may be of formula (Ia). In this embodiment, a metal carbonyl may suitably be used as the metal source. The metal may suitably be Fe, Ru, Co, Rh, Ir, Ni, Pd or Pt; for example Fe or Co. The process may, in this embodiment, suitably be carried out at 80° C. or higher, such as 90° C. or higher, such as −100° C. or higher, e.g. 105° C. or higher.

Preferably, the process is carried out under an inert atmosphere, for example a $N_2$ atmosphere. Suitably, dry solvents are used.

The present invention further provides, in a twenty-fourth aspect, a dehydration process comprising the steps of:
(a) providing a compound to be dehydrated; and
(b) adding LiX or $MgX_2$ to the compound, under aprotic conditions, wherein X is selected from F, Cl, Br and I, and each X may be the same or different.

Preferably, the dehydrating agent is selected from LiCl and $MgCl_2$.

Preferably, step (b) is carried out in an aprotic solvent. Preferably, the aprotic solvent is DMSO.

This process is particularly beneficial for dehydrating acid sensitive compounds, as it does not require the presence of acid.

For example, the process of this aspect may be used to dehydrate compounds comprising allylic alcohols and compounds comprising tertiary allylic groups. This process may, for example, be used to prepare the permethylcyclopentadiene precursor Cp*H and 1,2,3,4,5,6,7,8-octamethyl-9-methylene-9H-fluorene from their corresponding hydroxyl precursors, as well as preparing a substituted pentalene of formula (Ib) as described above.

The present invention will be further described by means of the following, non-limiting, examples.

EXAMPLES

Example 1

Preparation of 1,2,3,4,5,6-hexamethyl-1,2-dihydropentalene

All solvents were used as received and the reactions performed in air unless otherwise stated.

1.1 Synthesis of 2,4,6,8-tetramethyl-(tetramethyl-3, 7-dihydroxybicyclo[3.3.0]octa-2,6-diene-2,4,6,8-tetracarboxylate) (Formula II, where R1, R3, R4 and R6 are Me and A is $CO_2Me$)

To a 3 L three-necked round bottomed flask equipped with a mechanical stirrer and reflux condenser was added a solution of tetramethyl-3,7-dihydroxybicyclo[3.3.0]octa-2,6-diene-2,4,6,8-tetracarboxylate (100 g, 0.27 mol) in acetone (1300 ml), $K_2CO_3$ (336 g, 2.43 mol) and MeI (151 ml, 2.43 mol). Within 1 hr the granular appearance of the $K_2CO_3$ began to disperse and a fine white suspension resulted, along with the evolution of heat to maintain a gentle reflux. The mixture was stirred for 24 hr by which time it had cooled to room temperature. The temperature was then raised to 50° C. for 24 hr.

The mixture was cooled and then filtered through celite on a large sintered frit. The solids were washed with acetone (3×330 ml) and the volatiles removed from the solution by rotary evaporation to leave a pale yellow semi-solid. Redissolution in $CH_2Cl_2$ (500 ml) and filtering was used to remove traces of KI by-product.

Removal of the solvent to 10 mbar produced 2,4,6,8-tetramethyl-(tetramethyl-3,7-dihydroxybicyclo[3.3.0]octa-2,6-diene-2,4,6,8-tetracarboxylate) in almost quantitative yield (112.8 g, 0.26 mol, 98%) as a white to pale yellow solid.

Elemental analysis found (calculated) for $C_{20}H_{26}O_{10}$ (MW=426.15) (%): C 56.33 (56.33), H 6.13 (6.15)

HRMS (FI): m/z=426.1526 (426.1523) ($M^+$, 100%)

IR ($CH_2Cl_2$, $\nu_{CO}$): 1773 (vs), 1724 (vs)

$^1H$ NMR (300 MHz, $CDCl_3$, 329 K): δ 1.69 (12H, s); 2.82 (2H, s); 3.56 (12H, s)

$^{13}$C NMR {$^1$H} (75 MHz, CDCl$_3$, 329 K): δ 28.3 [MeC(CO$_2$Me)]; 52.2 [MeC(CO$_2$Me)]; 53.5 [MeC(CO$_2$Me)]; 58.3 (CH); 171.1 (CO$_2$Me); 204.1 (C=O)

1.2 Synthesis of 2,4,6,8-tetramethylbicyclo[3.3.0]octane-3,7-dione (Formula III, where R1, R3, R4 and R6 are Me)

2,4,6,8-tetramethyl-(tetramethyl-3,7-dihydroxybicyclo [3.3.0]octa-2,6-diene-2,4,6,8-tetracarboxylate) (112.8 g, 0.26 mol) was placed in a 1 L round bottomed flask charged with a large magnetic stirrer bar and concentrated HCl$_{(aq)}$ (600 ml) was added. This led to the slow dissolution of the organic material and produced a yellow solution in which slow effervescence was observed. A reflux condenser was added (equipped with an outlet tube to vent HCl$_{(g)}$ into a good extraction system) and the solution heated to 110° C. for 5 days. On the third, fourth and fifth days the reaction was cooled and 50 ml more of HCl$_{(aq)}$ was added to replenish HCl lost from the system, before heating again.

After completion, the reaction was cooled to room temperature whereupon copious amounts of a crystalline solid deposited from the liquid. The contents were poured into CH$_2$Cl$_2$ (500 ml) and the flask washed out with more solvent. The aqueous layer was separated and extracted with CH$_2$Cl$_2$ (2×500 ml) and the organic layers were combined and finally washed with water (2×200 ml). The orange-brown solution was then decolourised with activated charcoal (typically 30 g required) and dried over MgSO$_4$ before filtering. The volatiles were removed from the resultant clear solution to furnish 2,4,6,8-tetramethylbicyclo[3.3.0]octane-3,7-dione as a flaky off-white solid (49.5 g, 0.255 mol, 98%).

Elemental analysis found (calculated) for C$_{12}$H$_8$O$_2$ (MW=194.13) (%): C 74.29 (74.19), H 9.37 (9.34)

MS (FI): m/z=194.1303 (194.1307) (M$^+$, 100%)

IR (CH$_2$Cl$_2$, ν$_{CO}$): 1731 (vs)

$^1$NMR (300 MHz, CDCl$_3$, 300 K): δ 1.15 (6H, d, $^3$J$_{HH}$=6.9 Hz); 1.16 (6H, d, 7.5 Hz); 1.70 (2H, m, MeCH); 2.46 (2H, m, bridgehead CH); 2.58 (2H, m, MeCH)

$^{13}$C NMR (75 MHz, CDCl$_3$, 300 K): δ 10.7, 16.7 (MeCH); 43.6 (bridgehead-CH); 47.2, 47.4 (MeCH); 221.3 (C=O)

1.3 Synthesis of 2,4,6,8-tetramethylbicyclo[3.3.0] octa-1,5-diene-3,7-dione (Formula IV where R1, R3, R4 and R6 are Me)

2,4,6,8-tetramethylbicyclo[3.3.0]octane-3,7-dione (60 g, 0.31 mol) was dissolved in MeOH (650 ml) in a three-necked 2 L round bottomed flask containing a large stirrer bar, and equipped with a reflux condenser and dropping funnel. The solution was warmed to 50° C. and a few drops of Br$_2$ were then added to initiate the reaction, as evidenced by the disappearance of the orange colour of the halogen. The heating bath was removed and the remainder of the Br$_2$ (40 ml, 0.78 mol) was then added dropwise from the funnel so as to maintain reflux. An outlet tube to an adequate extraction system is recommended to vent the HBr$_{(g)}$ produced. The solution took on a dark brown appearance towards the latter stages of the reaction.

After addition was complete the solution was cooled and then poured into water (1.5 L) and CH$_2$Cl$_2$ (500 ml). The layers were separated and the aqueous layer was extracted with more CH$_2$Cl$_2$ (3×200 ml) until a vivid green colouration was achieved. The organic layers were combined and washed with 10% Na$_2$S$_2$O$_3$ (2×100 ml) and then saturated NaHCO$_3$ $_{(aq)}$ until the washings were just neutral. The extracts were then dried over MgSO$_4$, filtered and the solvent removed on a rotary evaporator to leave a thick red-brown oil which crystallises slowly on standing.

Distillation was achieved on a high-vacuum line (bath temperature 100° C., 10$^{-6}$-10$^{-7}$ mbar), collecting the liquid fraction at 70-85° C. The material also sublimes under these conditions and gentle heating of the glassware to keep the substance in the liquid phase was carried out, using a short Vigreux column to prevent decomposition through long residence times at high temperatures. Crystallisation occurred on cooling to room temperature and the pale yellow or orange solid was identified as 2,4,6,8-tetramethylbicyclo[3.3.0]octa-1,5-diene-3,7-dione (44.2 g, 0.232 mol, 75%), sufficiently pure for use in further reactions.

Elemental analysis found (calculated) for C$_{12}$H$_{14}$O$_2$ (MW=190.11) (%): C 75.64 (75.76), H 7.54 (7.42)

HRMS (FI): m/z=190.0995 (190.0994) (M$^+$, 100%)

IR (CH$_2$Cl$_2$, ν$_{CO,C=C}$): 1642 (s), 1708 (vs)

$^1$H NMR (300 MHz, CDCl$_3$, 300 K): δ 1.33 (6H, d, $^3$H$_{HH}$=7.8 Hz); 1.92 (6H, s); 3.07 (2H, q, $^3$H$_{HH}$=7.8 Hz)

$^{13}$C NMR {$^1$H} (75 MHz, CDCl$_3$, 300 K): δ 8.9 (MeCH); 13.0 (MeC=C); 40.1 (MeCH), 133.0 (MeC=C); 168.6 (MeC=C); 206.7 (C=O)

UV-Vis (MeOH): 287 (42,440)

1.4 Synthesis of 2,4,6,8-tetramethylbicyclo[3.3.0] octa-1(5)-ene-3,7-dione (Formula V where R1, R3, R4 and R6 are Me)

In a 250 ml three-necked round bottomed flask was charged 2,4,6,8-tetramethylbicyclo[3.3.0]octa-1,5-diene-3, 7-dione (15 g, 78.9 mmol), pyridine (80 ml), THF (80 ml) and activated Zn dust (20.5 g, excess). The mixture was thoroughly stirred and degassed with N$_2$ for 20 min at 0° C. before AcOH (30 ml) was added slowly, maintaining a reaction temperature of below 5° C. The pale yellow solution gradually decolourised and after addition was complete the reaction was allowed to warm to room temperature and stirred for 1 hr.

The suspension was then filtered to remove unreacted Zn, and the metal washed with CH$_2$Cl$_2$ (50 ml). The filtrate was then added to ice-cold 2M H$_2$SO$_{4(aq)}$ (prepared from 20.5 ml c.H$_2$SO$_4$ and 1050 ml water) with vigorous stirring, and this solution was extracted with CH$_2$Cl$_2$ (3×250 ml). The organic layers were combined, washed with water several times to raise the pH to neutrality, and then finally with saturated NaHCO$_{3(aq)}$ (150 ml).

This solution was then dried over MgSO$_4$, filtered, and the volatiles removed. The pale pink oily residue was distilled at high-vacuum (60-75° C., 10$^{-7}$ mbar) in the same manner as described in Example 1.3 above, and the distillate crystallised at room temperature. This material was identified as 2,4,6,8-tetramethylbicyclo [3.3.0]octa-1(5)-ene-3,7-dione (10.8 g, 56.2 mmol, 71.2% yield).

Elemental analysis found (calculated) for C$_{12}$H$_{16}$O$_2$ (MW=192.11) (%): C 74.85 (74.97), H 8.39 (8.39)

HRMS (EI): m/z=192.1141 (192.1150) (M$^+$, 100%)

IR (CH$_2$Cl$_2$, ν$_{CO}$): 1743 (vs)

$^1$H NMR (500 MHz, CDCl$_2$, 300 K): δ 1.14-1.24 (12H, several overlapping doublets); 2.90-3.10 (4H, several overlapping quartets)

$^{13}$C NMR {$^1$H} (125 MHz, CDCl$_3$, 300 K): δ 13.6, 14.0, 14.1, 14.2, 15.3, 15.7, 15.9 (MeCH); 43.8, 44.1, 44.2, 44.7, 45.7, 46.1, 46.2, 46.5 (MeCH); 144.4, 145.0, 145.5, 146.0 (C=C); 220.2, 220.3, 220.5, 220.6 (C=O)

1.5 Synthesis of 1,2,3,4,5,6-hexamethyl-1,2-dihydropentalene (Formula Ia where R1, R2, R3, R4, R5 and R6 are Me)

The following reaction was performed under $N_2$ with dry solvents when organometallic reagents are used. 'MeCeCl$_2$' (three equivalents per mole of diketone) was formed by the addition of MeLi.LiBr (1.5M in Et$_2$O, 20.6 ml, 30.9 mmol) to activated CeCl$_3$ (7.61 g, 30.9 mmol) in THF (100 ml) rapidly stirred at −78° C. The mixture was kept at this temperature for 1 hr.

A yellow suspension of the 'MeCeCl$_2$' in THF was prepared in a three-necked 2 L round bottomed flask, fitted with a sidearm Rotaflo tap and equipped with a mechanical stirrer (23.4 mmol 'MeCeCl$_2$' in 750 ml THF). To this suspension a solution of 2,4,6,8-tetramethylbicyclo[3.3.0]octa-1(5)-ene-3,7-dione (15 g, 78.1 mmol) in THF (100 ml) was added very slowly, maintaining an efficient stirring rate, at −78° C. The colour of the reaction gradually changed to a yellow-brown and after addition the whole was allowed to warm to room temperature over 1 hr.

The mixture was then poured into saturated NH$_4$Cl$_{(aq)}$ (750 ml), filtered through Celite and extracted with Et$_2$O (3×300 ml). After washing with water (150 ml) the solution was dried over MgSO$_4$ and the solvent removed to leave a white semi-solid residue that was taken into CHCl$_3$ (30 ml). This was then added to c.H$_2$SO$_4$ (5 ml) with stirring in a 100 ml round bottomed flask whereupon the mixture turned deep green. This was then transferred dropwise to a rapidly stirred solution of Na$_2$CO$_3$ (40 g in 500 ml water), and the colour was immediately discharged.

This aqueous mixture was then extracted with pentane (3×100 ml), the organic layers combined and dried over MgSO$_4$, and then filtered. The brown solution was then concentrated by rotary evaporation and finally distilled (65° C., 10$^{-3}$ mbar) as a vivid orange oil. This was identified as 1,2,3,4,5,6-hexamethyl-1,2-dihydropentalene along with another very minor impurity which could neither be identified nor separated, even by extensive chromatography (8.82 g, 46.9 mmol, approximately 60%).

HRMS (FI) for C$_{14}$H$_{20}$ (MW=188.1564): m/z=188.1561 (M$^+$, 100%)

IR (CCl$_4$): 2963 (m), 2927 (m), 2869 (m), 1550 (br), 1253 (s), 1218 (s), 1005 (5), 749 (br)

$^1$H NMR (300 MHz, CHCl$_3$, 300 K): δ 1.17 (3H, d, $^3$J$_{HH}$=7.2 Hz); 1.22 (3H, d, 7.2 Hz); 1.87 (3H, s); 1.88 (3H, s); 2.05 (3H, s); 2.06 (3H, s); 2.46 (2H, d of q); 2.58 (2H, d of q)

$^{13}$C NMR {$^1$H} (125 MHz, C$_6$D$_6$, 300 K): δ 11.4, 11.6, 13.7 (MeC=C, two overlapping); 18.0, 19.1 (MeCH); 39.8, 60.4 (MeCH); 116.3, 124.2, 144.8, 146.1, 147.5, 149.1 (quat-C)

UV-Vis (Et$_2$O): 260

Example 2

Synthesis of 1,2,3,4,5,6-hexamethyl-1,2-dihydropentalen-2-ol (Formula Ic) and 1,3,4,5,6-pentamethyl-2-methylene-1,2-dihydro-pentalene (Formula Ib)

All solvents were used as received and the reactions performed in air, except that the reaction was performed under N$_2$ with dry solvents when organometallic reagents were used.

A stirred suspension of 'MeCeCl$_2$' (23.7 mmol in 750 ml THF) was prepared as in Example 1.5 above, in a three-necked 2 L round bottomed flask fitted with a sidearm Rotaflo tap and equipped with a mechanical stirrer. To this suspension was added, dropwise, a solution of 2,4,6,8-tetramethylbicyclo[3.3.0]octa-1,5-diene-3,7-dione (15 g, 78.9 mmol) in THF (150 ml) at −78° C. The addition was centred into the vortex of stirring (otherwise a purple colouration developed which indicated decomposition of 2,4,6,8-tetramethylbicyclo[3.3.0]octa-1,5-diene-3,7-dione by enolisation, especially where the temperature of the medium is higher than −78° C.).

When an aliquot was quenched with water at this temperature, 1,2,3,4,5,6-hexamethyl-1,2,4,5-tetrahydropentalene-2,5-diol was the sole organic species present.

The suspension changed to a brown colour and when addition was complete the reaction was warmed slowly to 10°. At this point the mixture was poured into saturated NH$_4$Cl$_{(aq)}$ (750 ml), and the organic layer became a vivid orange which contained 1,2,3,4,5,6-hexamethyl-1,2-dihydropentalen-2-ol.

MS (FI) for C$_{14}$H$_{20}$O (MW=204.15): m/z=203.97 (M$^+$, 100%)

IR (CCl$_4$): 3609 (s), 2972 (m), 2929 (m), 2915 (m), 2915 (m), 2860 (m), 1551 (br), 1252 (s), 1217 (s), 1006 (s), 980 (s), 775 (br)

$^1$H NMR (300 MHz, DMSO-d$_6$, 300 K): δ 0.99 (3H, d, $^3$H$_{HH}$=7.2 Hz); 1.20 (3H, s); 1.76 (3H, s), 1.78 (3H, s); 1.94 (3H, s); 1.98 (3H, s); 2.65 (1H, q, $^3$J$_{HH}$=7.2 Hz); 4.70 (1H, s, OH)

$^{13}$C NMR {$^1$H} (75 MHz, DMSO-d$_6$, 300 K): δ 11.2, 11.3, 11.4, 15.3 (MeC=C); 26.8 [MeC(OH)]; 42.0 [MeC(OH)]; 88.5 (MeCH); 116.5, 123.8, 142.2, 144.8, 146.1, 150.2 (quat-C)

UV-Vis (Et$_2$O): 265

Filtration of the whole mixture through Celite was carried out, followed by washing the solid with Et$_2$O until free from any orange colouration. The aqueous layer was then extracted with more Et$_2$O (3×300 ml), subsequently the organic layers were combined and washed with water (200 ml) and then saturated NaHCO$_{3(aq)}$ (100 ml). After drying with MgSO$_4$ and filtering, the solvent was concentrated to 250 ml and DMSO (pre-dried over 3 Å molecular sieves, 150 ml) was added.

The remaining Et$_2$O was then stripped away on a rotary evaporator down to 10 mbar. The resulting DMSO solution of 1,2,3,4,5,6-hexamethyl-1,2-dihydropentalen-2-ol was transferred to a 1 L round bottomed flask charged with more DMSO (600 ml), LiCl (15 g) and a stirrer bar. The top was stoppered with a 'Suba seal' and a stream of N$_2$ gas was admitted through a cannula to flush the vessel of oxygen. The mixture was then stirred and heated to 85-90° C. during which time the colour changed to a deep red-brown. Aliquots were removed every 30 min and quenched with water, extracted with Et$_2$O and DMSO-d$_6$ (0.6 ml) added before rotary evaporation as described previously.

When the dehydration of the 1,2,3,4,5,6-hexamethyl-1,2-dihydropentalen-2-ol) was judged to be complete by $^1$H NMR (disappearance of OH resonance at δ=4.6 ppm), the solution was cooled to room temperature and poured onto ice (750 g) and Et$_2$O (200 ml) with stirring. Once the ice had melted the layers were separated and the aqueous layer was extracted with Et$_2$O (2×150 ml). The organic layers were combined and washed with saturated NaHCO$_{3(aq)}$ (1×100 ml) to remove any traces of acid.

The dark red solution was then dried over MgSO$_4$, filtered and reduced in volume to 150 ml. At this point it was transferred to a medium Schlenk tube containing CaH$_2$ (5 g) and was degassed using a stream of N$_2$ for 20 min. The vessel was then opened to the nitrogen manifold on a vacuum line apparatus and stirred for 48 hr before filtering via cannula to a fresh medium Schlenk tube, to give a solution of 1,3,4,5,6-pentamethyl-2-methylene-1,2-dihydro-pentalene.

HRMS (FI) for $C_{14}H_{18}$ (MW=186.1400): m/z=186.1409 ($M^+$, 100%)

IR ($CCl_4$): 2965 (m), 2857 (m), 2685 (m), 1625 (s), 1550 (br), 1444 (s), 945 (s), 740 (br)

$^1$H NMR (300 MHz, DMSO-$d_6$, 300 K): δ 1.18 (3H, d, $^3J_{HH}$=6.9 Hz); 1.82 (6H, s); 1.99 (3H, s); 2.08 (3H, s); 3.26 (1H, q, $^3J_{HH}$=6.9 Hz); 5.09 (1H, s); 5.21 (1H, s)

$^{13}$C NMR {$^1$H} (75 MHz, CDCl$_3$, 300 K): δ 11.2, 11.3, 11.5, 11.7 (MeC=C); 18.9 (MeCH); 34.8 (MeCH); 105.6 (C=CH$_2$); 117.2, 124.1, 140.9, 141.7, 147.8, 152.6 (quat-C) 164.2 (C=CH$_2$)

UV-Vis (Et$_2$O): 294, 303

Example 3

Synthesis of Li(Pn*H) (Formula Ie)

The synthesis was conducted under a N$_2$ atmosphere and using dry solvents.

The solution of 1,3,4,5,6-pentamethyl-2-methylene-1,2-dihydro-pentalene prepared in Example 2 was treated with LS-Selectride (1.0M in THF, 51.3 ml, 51.3 mmol) at room temperature. The solution started to form a fine precipitate within 1 hr and stirring was continued for 48 hr in total.

After this time the suspension was filtered on a frit and washed with Et$_2$O (3×50 ml) and dried in vacuo for 8 hr. The resultant fine beige powder was identified as Li(Pn*H) (9.19 g, 47.3 mmol, 60% based on 2,4,6,8-tetramethylbicyclo[3.3.0]octa-1,5-diene-3,7-dione, 92% based on LS-selectride). $^1$H NMR spectroscopy (C$_6$D$_6$) of the supernatant confirmed the complete consumption of 1,3,4,5,6-pentamethyl-2-methylene-1,2-dihydro-pentalene.

IR (KBr): 2959 (m), 2912 (m), 2855 (m), 1616 (w), 1443 (s), 1420 (s), 1383 (s), 1095 (m), 1069 (m), 1022 (m), 669 (m), 501 (br)

$^1$H NMR (300 MHz, pyridine-$d_5$, 300 K): δ 1.45 (3H, d, $^3J_{HH}$=6.6 Hz); 2.00 (3H, s); 2.20 (3H, s); 2.31 (3H, s); 2.37 (3H, s); 2.47 (3H, s); 3.14 (1H, broad)

$^{13}$C NMR {$^1$H} (75 MHz, pyridine-$d_5$, 300 K): δ 11.5, 12.1, 12.3, 12.6, 13.2 (Me-Cp and MeC=C); 18.2 (MeCH); 42.4 (MeCH); 99.0, 103.9, 109.8, 125.9, 130.4, 131.3 (quat-C); one quaternary-C unresolved from solvent resonance

Example 4

Synthesis of Li(Pn*$^t$H)(DME)$_x$ (Formula If)

The synthesis was conducted under a N$_2$ atmosphere and using dry solvents.

1,2,3,4,5,6-hexamethyl-1,2-dihydropentalene (1.5 g, 7.96 mmol) was dissolved in pentane (50 ml) and DME (0.72 ml, 8 mmol) added before cooling to −78° C. Li$^n$Bu (2.5M in hexane, 4 ml, 10 mmol) was added dropwise to this solution after which the reaction was allowed to warm to room temperature.

Above 0° C. a buff precipitate started to form, and the reaction was stirred for 14 hr. The suspension was filtered on a frit and washed with pentane (3×30 ml) and then dried in vacuo for 3 hr. This afforded Li(Pn*$^t$H)(DME)$_x$ (0.93 g, 4.78 mmol, 63%) as a pyrophoric powder; x was found to be between 0.2 and 0.3 as ascertained by $^1$H NMR.

IR (KBr): 2957 (m), 2923 (m), 2770 (m), 1655 (s), 1449 (br), 1369 (m), 1077 (5), 591 (br), 535 (br)

$^1$H NMR (300 MHz, THF-$d_8$, 300 K): δ 1.13 (3H, d, $^3J_{HH}$=6.6 Hz); 1.17 (3H, d, $^3J_{HH}$=6.3 Hz); 1.87 (3H, s); 1.89 (3H, s); 2.03 (3H, s); 2.3-2.5 (2H, broad m); 3.27 (6H, s, DME); 3.42 (4H, s, DME); 3.96 (1H, s); 4.33 (1H, s)

Example 5

Synthesis of Li$_2$Pn*(TMEDA)$_x$ (Formula Ig)

The synthesis was conducted under a N$_2$ atmosphere and using dry solvents.

Li(Pn*H) (13.60 g, 70.1 mmol) was suspended in hexane (250 ml) in a 500 ml round bottomed flask equipped with a sidearm, Rotaflo tap and reflux condenser. TMEDA (3.16 ml, 21.0 mmol), Li$^n$Bu (2.5M in hexane, 33.6 ml, 84.1 mmol) and a glass-coated stirrer bar were then added, followed by reflux for 3 days. After this time the suspension had darkened in colour. The suspension was then filtered through a low porosity frit and the solid was washed with hexane (3×100 ml) until the washings were colourless.

Drying of this material in vacuo for 6 hr gave a dark brown powdery solid, Li$_2$Pn*(TMEDA)$_x$, (15.61 g, 69.0 mmol, 97%, x=0.23). The value of x can be determined from reaction of Li$_2$Pn*(TMEDA)$_x$ with Me$_3$SnCl in C$_5$D$_5$ followed by the addition of pyridine-$d_5$ to solubilise LiCl, and deduced by comparison of the integrations from (SnMe$_3$)$_2$Pn* and free TMEDA in the $^1$H NMR spectrum; it typically varies between 0.15-0.25.

IR (KBr): 2958 (m), 2911 (m), 2855 (m), 1457 (s), 1434 (s), 1097 (br), 1019 (5), 541 (br)

$^1$H NMR (300 MHz, THF-$d_8$, 300 K): δ 1.98 (6H, s); 2.04 (12H, s, TMEDA); 2.19 (4H, s, TMEDA); 2.35 (12H, s)

$^{13}$C {$^1$H} NMR (75 MHz, THF-$d_8$, 300 K): δ 11.2 (C6); 13.0 (C5, C7); 46.1 (TMEDA); 58.6 (TMEDA); 84.1 (C1, C3); 114.1 (C2); 119.02 (C4)

$^7$Li NMR (194 MHz, THF-$d_8$, 300K): δ −11.6, −12.1

Example 6

Synthesis of (SnMe$_3$)$_2$Pn* (Formula Id)

The synthesis was conducted under a N$_2$ atmosphere and using dry solvents.

To a stirred suspension of Li$_2$Pn*(TMEDA)$_x$ (x=0.23, 1.00 g, 4.40 mmol) in Et$_2$O (80 ml) was added a solution of Me$_3$SnCl (1.93 g, 9.7 mmol) in Et$_2$O (20 ml) at −78° C., followed by warming to room temperature. The solution immediately turned pale yellow and a fine precipitate of LiCl formed. Volatiles were removed in vacuo and the residue was extracted with pentane (2×40 ml) and filtered via cannula.

The solvent was then stripped to provide (SnMe$_3$)$_2$Pn* (2.22 g, 4.31 mmol, 98%) as a pale yellow crystalline solid which was determined pure by $^1$H NMR spectroscopy and shown to contain a mixture of E- and Z-isomers.

Elemental analysis found (calculated) for C$_{20}$H$_{36}$Sn$_2$ (MW=516.09) (%): C 46.81 (46.74), H 7.15 (7.06)

MS (EI): M/z=516.0852 (516.0861) ($M^+$, 2%); 351 ($M^+$-SnMe$_3$, 57%); 186 ($M^+$-2SnMe$_3$, 100%)

IR (KBr): 2973 (m), 2952 (m), 2910 (m), 2941 (m), 2860 (m), 1555 (w), 1455 (s), 1445 (s), 1394 (s), 1363 (s), 1279 (s), 1173 (s), 1050 (s), 757 (br), 529 (s), 515 (s), 500 (s)

$^1$H NMR (300 MHz, toluene-$d_8$, 173K, isomers a and b): δ −0.00 (18H, SnMe$_3$, $^3J_{SnH}$=50 Hz, E); 0.09 (18H, SnMe$_3$, $^3J_{SnH}$=50 Hz, Z); 1.64 [6H, s, (C9, C12), Z]; 1.73 [6H, s, (C9, C12), E]; 1.97 [6H, s, (C10, C13), E]; 1.99 [6H, s, (C10, C13), Z]; 2.21 [6H, s, (C11, C14), Z]; 2.25 [6H, s, (C11, C14), E]

$^{13}$C {$^1$H} NMR (75 MHz, toluene-$d_8$, 173 K): δ −9.1 (SnMe$_3$, $^1J_{SnC}$=308 Hz, E); −9.0 (SnMe$_3$, $^1J_{SnC}$=272 Hz, Z); 11.5 (C10, C13, Z); 11.7 (C10, C13, E); 12.3 (C11, C14, E and Z); 14.7 (C9, C12, E and Z); 50.0 (C1, C5, Z); 51.4 (C1, C5, E); 124.3 (C3, C7, E); 126.2 (C3, C7, Z); 137.1 (C2, C6, E); 138.2 (C2, C6, Z); 147.8 (C4, C8, E); 150.8 (C4, C8, Z)

$^{119}$Sn NMR {$^1$H} NMR (112 MHz, toluene-d$_8$, 173 K): δ 39.4 (E); 41.4 (Z)

The structure of the product was characterised by X-Ray crystal diffraction.

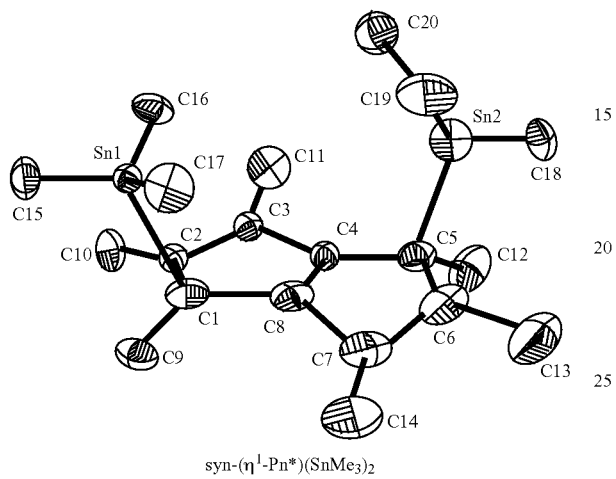

syn-(η$^1$-Pn*)(SnMe$_3$)$_2$

Example 7

Synthesis of Li$_2$Pn*(TMEDA)$_2$ (Formula Ig)

The synthesis was conducted under a N$_2$ atmosphere and using dry solvents.

(SnMe$_3$)$_2$Pn* (0.30 g, 0.58 mmol) was dissolved in TMEDA (10 ml) to give a pale yellow solution. Halide-free LiMe (1.6 Min Et$_2$O, 0.76 ml, 1.20 mmol) was then added at room temperature to this solution, whereupon then colour changed to orange and then dark red over 1 min, and a microcrystalline solid began to precipitate.

Warming led to redissolution of this material and slow cooling to −35° C. over 24 hr provided dark orange prisms. Decantation of the supernatant followed by washing with Et$_2$O (10 ml) and drying under a flush of N$_2$ gave Li$_2$Pn* (TMEDA)$_2$ (0.195 g, 0.45 mmol, 78%) as an extremely air-sensitive orange powder which readily loses coordinated TMEDA.

IR (KBr): 2958 (m), 2911 (m), 2855 (m), 1457 (s), 1434 (s), 1097 (br), 1019 (s), 541 (br)

$^1$H NMR (300 MHz, THF-d$_8$, 300 K): δ 1.98 (6H, s); 2.04 (12H, s, TMEDA); 2.19 (4H, s, TMEDA); 2.35 (12H, s)

$^{13}$C {$^1$H} NMR (75 MHz, THF-d$_8$, 300 K): δ 11.2 (C6); 13.0 (C5, C7); 46.1 (TMEDA); 58.6 (TMEDA); 84.1 (C1, C3); 114.1 (C2); 119.02 (C4)

$^7$Li NMR (194 MHz, THF-d$_8$, 300K): δ −11.6, −12.1

The structure of the product was characterised by X-Ray crystal diffraction.

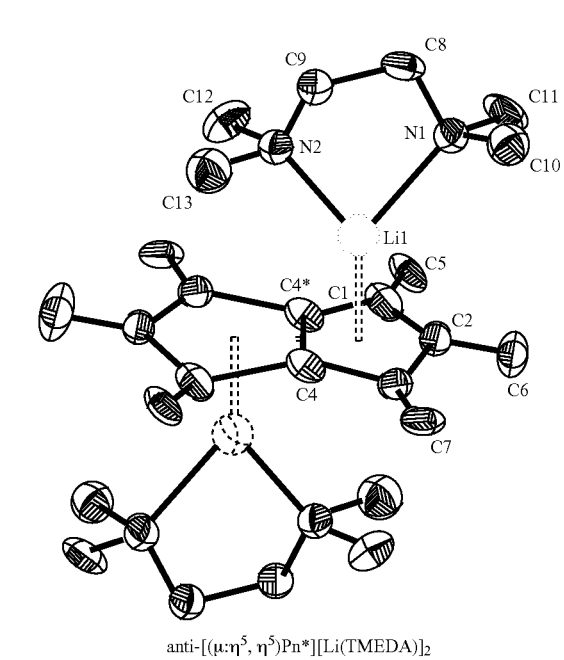

anti-[(μ:η$^5$, η$^5$)Pn*][Li(TMEDA)]$_2$

Example 8a

Synthesis of [Fe$_2$(CO)$_4$(μ-CO)](μ:η$_5$, η$^5$-Pn*)

The synthesis was conducted under a N$_2$ atmosphere and using dry solvents.

To a solution of 1,3,4,5,6-pentamethyl-2-methylene-1,2-dihydro-pentalene (1.50 g, 8.05 mmol) in Et$_2$O was added toluene (60 ml). The volume of solvent was reduced in vacuo to 50 ml. Fe$_2$(CO)$_9$ (4.40 g, 12.1 mmol) was then added against a flush of N$_2$. The suspension was then heated to reflux, whereupon the solids dissolved and the colour changed to red-brown.

After 24 hr the reaction was cooled and another portion of Fe$_2$(CO)$_9$ (5.00 g, 13.7 mmol) added, then reflux was resumed. 24 hr later the mixture was cooled, filtered through Celite on a frit and the solvent removed under reduced pressure. The dark red residue was then washed with cold (0° C.) pentane (3×50 ml) to leave a dark brown solid.

This residue was then recrystallised from toluene:hexane (2:1, 70 ml) at −80° C. to provide [Fe$_2$(CO)$_4$(μ-CO)](μ:η$^5$, η$^5$-Pn*) as a brown microcrystalline material after two crops (1.59 g, 3.62 mmol, 45%).

Elemental analysis found (calculated) for C$_{19}$H$_{18}$O$_5$Fe$_2$ (MW=432.03) (%): C 52.17 (52.10), H 4.22 (4.14)

HRMS (EI): m/z=437.9867 (437.9853) (M$^+$, 6%); 410 (M$^+$-CO, 18%); 382 (M$^+$-2CO, 8%); 354 (M$^+$-3CO, 27%); 326 (M$^+$-4CO, 68%); 298 (M$^+$-5CO, 100%)

IR (CH$_2$Cl$_2$, ν$_{CO}$): 2014, 1980, 1947, 1750 [all (s)]

IR (KBr): 2963 (m), 2923 (m), 2862 (m), 2006 (s), 1969 (s), 1950 (s), 1922 (s), 1750 (s), 1472 (m), 1380 (m), 1020 (m), 634 (s)

$^1$H NMR (300 MHz, C$_6$D$_6$, 300 K): δ 1.35 (12H, s); 1.43 (6H, s)

$^{13}$C {$^1$H} NMR (75 MHz, C$_6$D$_6$, 300 K): δ 10.0 (C9, C11); 10.3 (C10); 65.4 (C4, C8); 103.7 (C2); 105.7 (C1, C3); 226.7 (CO)

The complex may, for example, be used as a Fischer-Tropsch catalyst or a C—H bond activation catalyst, or a catalyst in olefin polymerisation.

Example 8b

Alternative Synthesis of [Fe$_2$(CO)$_4$(μ-CO)](μ:η$^5$, η$^5$-Pn*)

To a solution of 1,2,3,4,5,6-hexamethyl-1,2-dihydropentalene (0.50 g, 2.66 mmol) in toluene was added Fe$_2$(CO)$_9$ (2.90 g, 7.97 mmol) and the suspension was heated to 110° C. The solution became a deep red-brown and heating was continued for 24 hr.

The mixture was then cooled and a further portion of Fe$_2$(CO)$_9$ (2.90 g, 7.97 mmol) was added, followed by heating again to 110° C. for a remaining 24 hr. Thereafter the solution was cooled and then filtered through Celite to remove colloidal iron, the residue being washed three times with toluene.

The solvent was stripped in vacuo down to 30 ml and hexane (30 ml) was added. Cooling to −78° C. gave brown crystals of Fe$_2$(CO)$_5$Pn* which were filtered, washed with pentane and vacuum dried to yield 0.32 g (27.4%). A second crop was isolated after solvent volume reduction and further cooling to −78° C. (0.09 g, 7.7%).

The complex may, for example, be used as a Fischer-Tropsch catalyst or a C—H bond activation catalyst, or a catalyst in olefin polymerisation.

Example 9

Synthesis of [Co(CO)$_2$]$_2$(μ:η$^5$, η$^5$-Pn*)

The synthesis was conducted under a N$_2$ atmosphere and using dry solvents.

A solution of 1,3,4,5,6-pentamethyl-2-methylene-1,2-dihydro-pentalene (1.50 g, 8.05 mmol) in toluene (50 ml) was prepared as in Example 2. Co$_2$(CO)$_8$ (4.13 g, 12.07 mmol) was then added against a flush of N$_2$ and an immediate colour change to brown proceeded with evolution of gas. The solution was then refluxed for 24 hr, cooled and filtered through Celite.

The solvent was then removed under reduced pressure and the residue chromatographed on silica using hexane:toluene as eluent (80:20), collecting the first brown band. Removal of solvent gave [Co(CO)$_2$]$_2$(μ:η$^5$, η$^5$-Pn*) as a chocolate-brown solid (2.08 g, 4.99 mmol, 62%).

Elemental analysis found (calculated) for C$_{18}$H$_{18}$O$_4$Co$_2$ (MW=416.20) (%): C 51.84 (51.94), H 4.39 (4.36)

MS (EI): m/z=416.20 (M$^+$, 55%); 388 (M$^+$-CO, 85%); 360 (M$^+$-2CO, 100%); 332 (M$^+$-3CO, 45%); 304 (M$^+$-4CO, 90%); 186 (M$^+$-4CO-2Co, 15%)

IR (CH$_2$Cl$_2$, ν$_{CO}$): 2015, 1973, 1950 [all (s)]

$^1$H NMR (300 MHz, C$_6$D$_6$, 300 K): δ 1.36 (12H, s); 1.82 (6H, s)

$^{13}$C {$^1$H} NMR (75 MHz, C$_6$D$_6$, 300 K): δ 10.5 (C9, C11); 11.5 (C10); 68.7 (C4, C8); 102.1 (C2); 102.2 (C1, C3); 207.7 (CO)

The complex may, for example, be used as a Fischer-Tropsch catalyst or a C—H bond activation catalyst, or a catalyst in olefin polymerisation.

Characterisation

The products of Examples 8a, 8b and 9 were further characterised by X-Ray crystal diffraction.

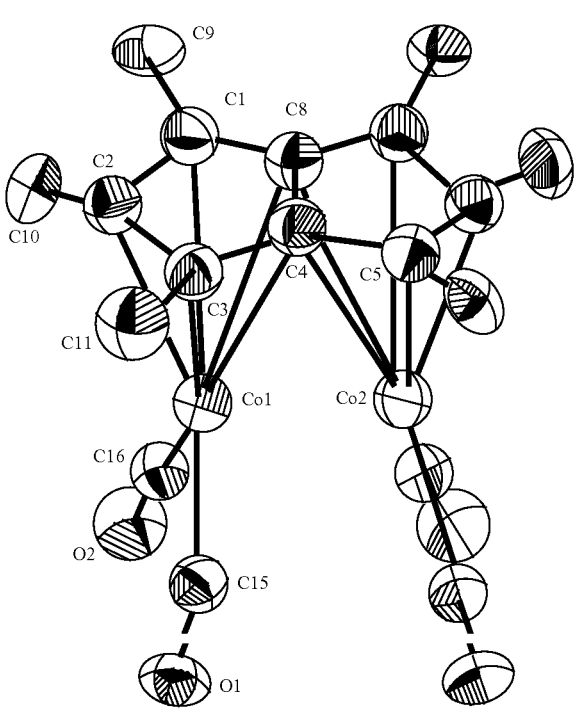

Example 9

(μ: η$^5$, η$^5$-Pn*)[Co(CO)$_2$]$_2$

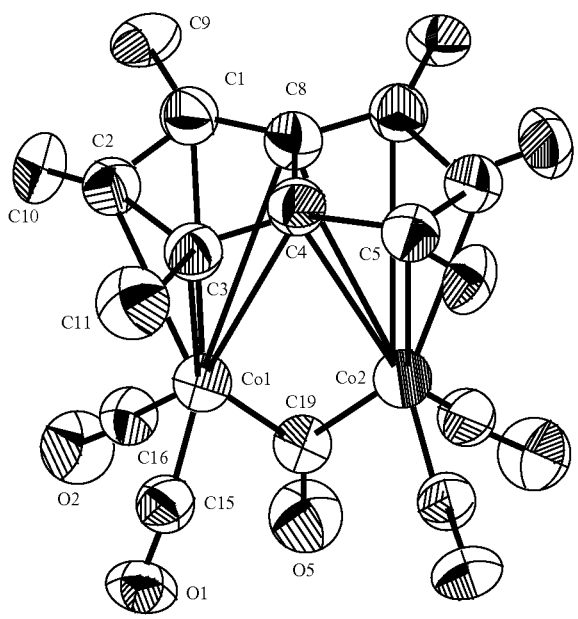

Example 8a, 8b (μ: η$^5$, η$^5$-Pn*)[Fe(CO)2]$_2$(μ-CO)

Example 10

Synthesis of Zr(Cp)(η⁸-Pn*)Cl

The synthesis was conducted under a $N_2$ atmosphere and using dry solvents.

A stirred suspension of $Li_2Pn^*(TMEDA)_x$ (x=0.23, 1.50 g, 6.61 mmol) in $C_6H_6$ (60 ml) was added slowly to a solution of $Zr(Cp)_2Cl_2$ (1.91 g, 6.61 mmol) in $C_6H_6$ (20 ml) and the mixture turned red. The reaction was stirred for 24 hr during which time it developed a brown coloration, and was then filtered through Celite on a frit. The solvent was stripped in vacuo to yield an oily residue, which was subjected to dynamic vacuum ($10^{-3}$ mbar) for 18 hr.

The resultant yellow-brown powder was scraped into a sublimation apparatus and sublimed at 120-140° C. ($10^{-7}$ mbar) to provide a yellow sublimate. Recrystallisation from toluene at −80° C. gave Zr(Cp)(η⁸-Pn)Cl (0.31 g, 0.82 mmol, 12%) as bright yellow needles.

Elemental analysis found (calculated) for $C_{19}H_{23}ClZr$ (MW=378.06) (%): C 60.43 (60.36), H 6.22 (6.13)

HRMS (EI): m/z=376.0552 (376.0535) (M⁺, 89%); 340 (M⁺-Cl, 100%); 311 (M⁺-Cp, 76%)

IR (KBr): 2963 (m), 2905 (m), 2862 (m), 1444 (br), 1383 (s), 1021 (s), 801 (s), 683 (s)

¹H NMR (300 MHz, $C_6D_6$, 300 K): δ 1.65 (6H, s); 1.76 (6H, s); 2.11 (6H, s); 5.65 (5H, s)

¹³C {¹H} NMR (75 MHz, $C_6D_6$, 300 K): δ 11.2, 12.5, 13.3 (C9, C10, C11); 105.6, 112.5 (C1, C3); 111.0 (Cp); 119.6 (C2); 125.8, 129.3 (C4, C8)

The structure of the product was characterised by X-Ray crystal diffraction.

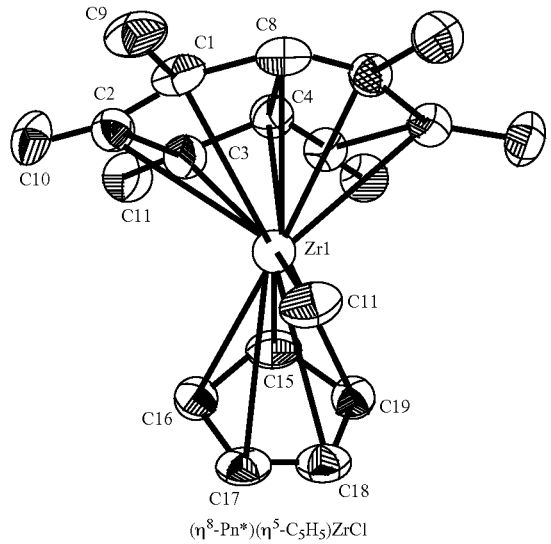

(η⁸-Pn*)(η⁵-C₅H₅)ZrCl

The complex may, for example, be used as a catalyst in α-olefin polymerisation.

Example 11

Synthesis of [Ti(η⁸-Pn*)Cl(μ-Cl)]₂

The synthesis was conducted under a $N_2$ atmosphere and using dry solvents.

$Li_2Pn^*(TMEDA)_x$ (x=0.23, 1.00 g, 4.40 mmol) in THF (20 ml) was added to a suspension of $TiCl_3$·3THF (1.62 g, 4.40 mmol) in THF (40 ml) at −78° C.). The mixture turned red and then green-brown upon warming to room temperature, after which it was stirred for 18 hr. The solution was then transferred onto $PbCl_2$ (0.61 g, 2.20 mmol) and the reaction stirred for a further 4 hr before the THF was removed under reduced pressure.

The oily solid was extracted with toluene (3×40 ml) and filtered via cannula and then the solvent was stripped in vacuo. Sublimation of this residue at 120-130° C. ($10^{-7}$ mbar) afforded an orange sublimate which could be recrystallised from hexane at −80° C. to give [Ti(η⁸-Pn*)Cl(μ-Cl)]₂ as a red-brown solid (0.12 g, 0.19 mmol, 8.6%).

Elemental analysis found (calculated) for $C_{14}H_{18}Cl_2Ti$ (MW=610.13) (%): C 54.98 (55.12), H 5.90 (5.95)

HRMS (EI): m/z=304.0263 (304.0265) (M⁺/2, 4%); 268 (M⁺/2-Cl, 40%); 186 (M⁺/2-Ti-2Cl)

IR (KBr): 2962 (m), 2913 (m), 2856 (m), 1645 (m), 1445 (s), 1377 (s), 1017 (s), 791 (m), 695 (m)

¹H NMR (300 MHz, $C_6D_6$, 300 K): δ 1.62 (6H, s); 1.89 (12H, s)

¹³C {¹H} NMR (75 MHz, $C_6D_6$, 300 K): δ 10.8 (C9, C11, C12, C14); 12.8 (C10, C13); 126.7 (C1, C3, C5, C7); 134.9 (C2, C6); 144.2 (C4, C8)

The structure of the product was characterised by X-Ray crystal diffraction.

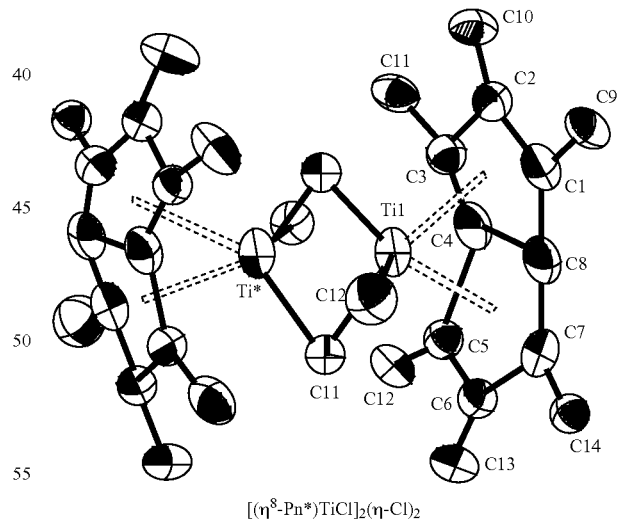

[(η⁸-Pn*)TiCl]₂(η-Cl)₂

The complex may, for example, be used as a catalyst in α-olefin polymerisation.

Example 12

Synthesis of Ce(η⁸-Pn*)₂

The synthesis was conducted under a $N_2$ atmosphere and using dry solvents.

To a mixture of Li$_2$Pn*(TMEDA)$_x$ (x=0.23, 1.79 g, 7.89 mmol) and CeCl$_3$(anh) (0.97 g, 3.94 mmol) was added pre-cooled THF (70 ml) at −78° C. in an ampoule equipped with a Rotaflo tap. The mixture was warmed slowly to room temperature before being heated to 65° C. for 24 hr. The brown solution (containing small amounts of particulate matter) was then cooled and taken into the glove-box.

1,2-dichloroethane (3.12 ml, 40.0 mmol) was then added with swirling resulting in an immediate colour change to an intense purple. The ampoule was then removed from the glove-box and the THF solvent removed in vacuo. The almost black residue was then extracted with CH$_2$Cl$_2$ (3×50 ml) and filtered through Celite on a sintered frit.

Stripping of the solvent under reduced pressure, washing with −78° C. pentane (2×20 ml) and subsequent sublimation of the resultant material at 190-220° C. (10$^{-7}$ mbar) gave Ce(η$^8$-Pn*)$_2$ as a dark purple-black solid (1.23 g, 2.40 mmol, 61%).

Elemental analysis found (calculated) for C$_{28}$H$_{36}$Ce (MW=512.70) (%): C 65.78 (65.59), H 7.15 (7.08)

HRMS (EI): m/z=512.1876 (512.1871) (M$^+$, 83%); 326 (M$^+$-Pn*); 186 (M$^+$-Pn*-Ce)

IR (KBr): 2957 (m), 2903 (m), 2852 (m), 1430 (br), 1379 (vs), 1222 (s), 1019 (s), 652 (s), 604 (s)

$^1$H NMR (300 MHz, C$_6$D$_6$, 300 K): δ 1.45 (6H, s); 6.20 (12H, s)

$^{13}$C {$^1$H} NMR (75 MHz, C$_6$D$_6$, 300 K): δ 2.5 (C9, C11, C12, C14); 11.8 (C10, C13); 108.5 (C2, C6); 129.5 (C4, C8); 149.9 (C1, C3, C5, C7)

UV-Vis (THF): 530 (17,000)

CV (THF, 0.1 M [$^n$Bu$_4$N]BF$_4$): E$_{1/2}$=−0.83 V (reversible)

The structure of the product was characterised by X-Ray crystal diffraction.

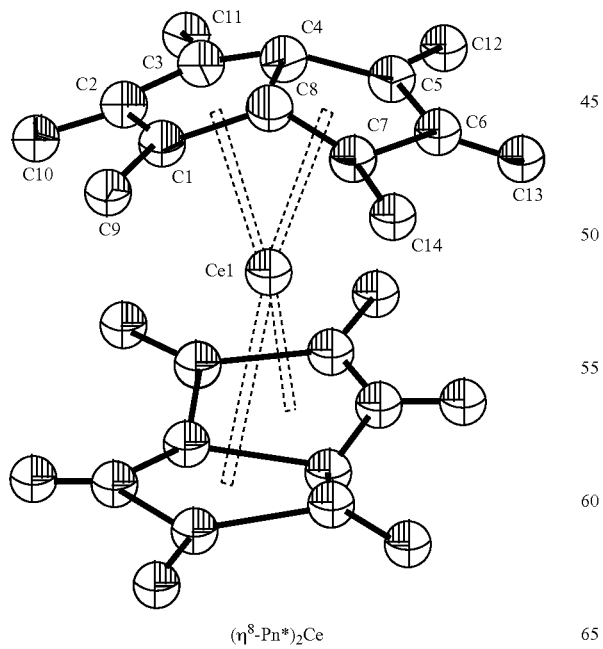

(η$^8$-Pn*)$_2$Ce

Example 13

Synthesis of [(η$^8$-Pn*)Ti]$_2$(μ-Cl)$_3$

[(η$^8$-Pn*)TiCl]$_2$(μ-Cl)$_2$ (0.350 g, 0.57 mmol) and potassium metal (0.045 g, 1.14 mmol) were stirred in C$_6$H$_6$ (20 ml) at 80° C. for 18 hours. The solvent was then removed under vacuum and the residue extracted with pentane, filtered and reduced in volume.

Cooling to −35° C. produced dark green crystals of the product. Yield: 46% (0.151 g).

The structure of the product was characterised by X-Ray crystal diffraction.

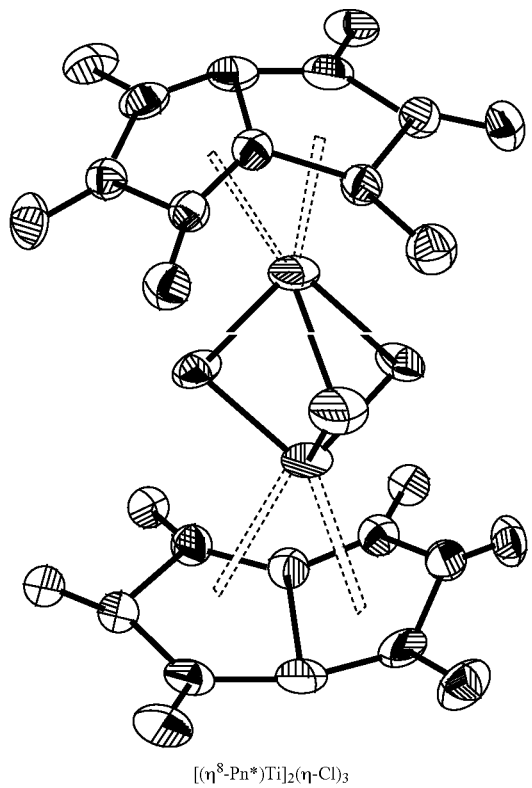

[(η$^8$-Pn*)Ti]$_2$(η-Cl)$_3$

The complex may, for example, be used as a catalyst in α-olefin polymerisation.

Example 14

Synthesis of [(μ:η$^5$, η$^3$-Pn*)Rh$_2$(CO)$_2$]$_2$(μ-CO)$_2$ (μ:η$^5$,η$^5$-Pn*)[Rh(CO)$_2$]$_2$ (prepared from equimolar amounts of cis-Pn*(SnMe$_3$)$_2$ and [Rh(CO)$_2$Cl]$_2$ in hexane) (0.350 g, 0.69 mmol) cyclopentane (40 ml) was photolyzed in a quartz Schlenk tube using a 500 W Hg lamp for 10 hours. The solution was then cooled to −35° C. producing dark orange crystals of the product, which were filtered and vacuum dried.

Yield: 87% (0.288 g). 1H NMR (C6D6, 300 MHz): δ 2.29 (6H, s, CH3), 1.83 (6H, s, CH3), 1.25 (6H, s, CH3). HRMS (EI): m/z calculated for $C_{34}H_{36}Rh_4O_6$ (M) 952.2680. found 952.2675.

The structure of the product was characterised by X-Ray crystal diffraction.

Yield: 21.1% (0.238 g, 0.49 mmol). Analysis Found (calculated) for $C_{28}H_{36}Mn_2$: C 69.64 (69.71); H 7.50 (7.52). 1H NMR (C7D8, 300 MHz): δ 59.76 (br, 12H, Δv1/2=766 Hz, CH3), −19.15 (br, 24H, Δv1/2=918 Hz, CH3). HRMS (EI): m/z calculated for $C_{28}H_{36}Mn_2$ (M) 482.1578. found 482.1578.

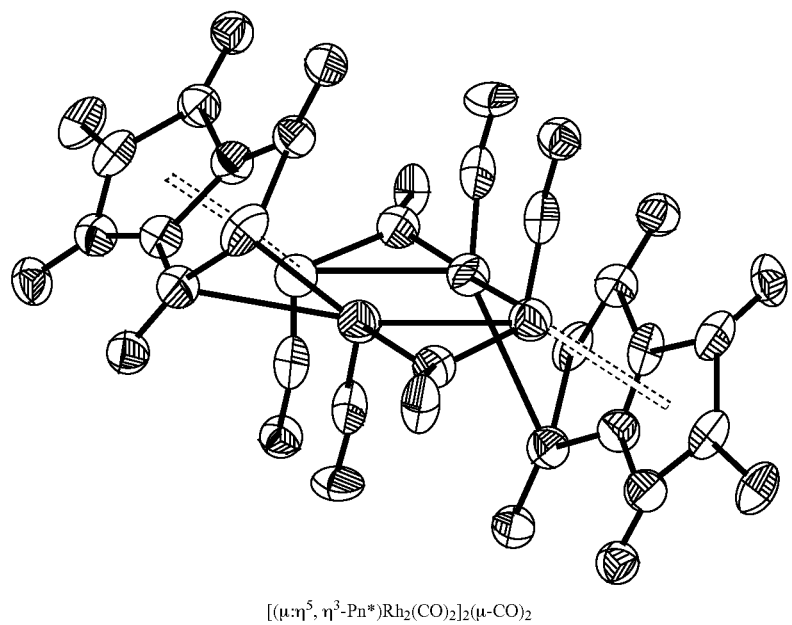

[(μ:η⁵, η³-Pn*)Rh₂(CO)₂]₂(μ-CO)₂

The complex may, for example, be used as a catalyst in olefin polymerisation or as a catalyst in C—H bond activation.

Example 15

Synthesis of Mn₂Pn*₂

MnCl₂ (0.58 g, 4.67 mmol) was stirred in THF (30 ml) at room temperature for 24 hours to form MnCl₂(THF)₁.₅. Li₂Pn*(TMEDA)₀.₁₂ (1.00 g, 4.67 mmol) in THF (20 ml) was then added whilst stirring at −78° C. and allowed to warm to ambient temperature, during which time the solution had turned green in colour. The volatiles were removed under reduced pressure and the residue subjected to dynamic vacuum (10-3 mbar) for 24 hours. The solid was then extracted with hexane (150 ml) using a Soxhlet apparatus to give the microcrystalline product (extremely air-sensitive) after cooling to room temperature, which was washed with cold toluene (−78° C.) and dried in vacuo.

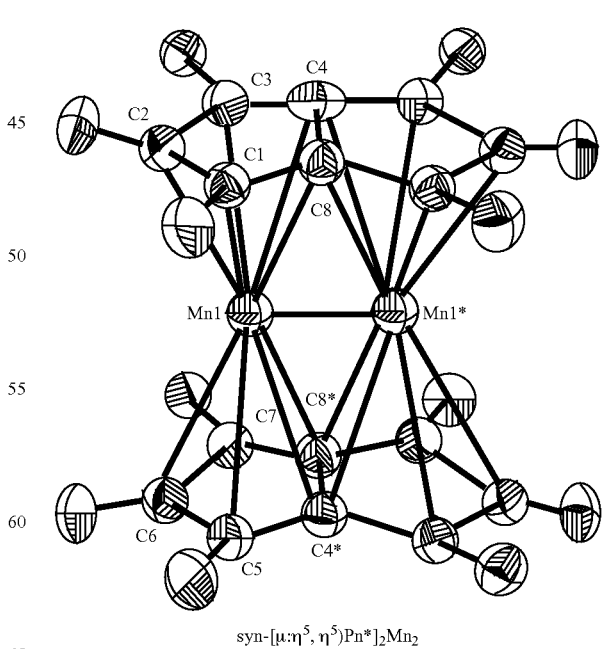

syn-[μ:η⁵, η⁵)Pn*]₂Mn₂

The complex may, for example, be used as an electron transfer material.

Example 16

Synthesis of Co$_2$Pn*$_2$

THF (40 ml) was added to a mixture of CoBr$_2$(DME) (0.60 g, 1.95 mmol) and cis-Pn*(SnMe$_3$)$_2$ (1.00 g, 1.95 mmol) whilst stirring at room temperature, the slurry rapidly turning green. After a further 24 hours the solution was filtered through Celite on a sintered frit and the solvent was stripped in vacuo to give a solid which was washed with pentane (2×20 ml). The remaining material was extracted with toluene (60° C., 3×30 ml), the filtrate reduced in volume to ca. 30 ml and cooled to −35° C. The product formed as dark green crystals, which were washed with cold toluene (−78° C.) and dried in vacuo.

Yield: 55.5% (0.529 g, 1.08 mmol). Analysis Found (calculated) for C$_{28}$H$_{36}$Co$_2$: C 68.24 (68.57); H 7.40 (7.40). 1H NMR (C7D8, 300 MHz): δ 1.93 (s, 24H, CH3), 1.41 (s, 12H, CH3). 13C{1H} NMR (C7D8, 75 MHz): δ 97.8 (s, ring-C); 90.5 (s, ring-C); 53.0 (s, ring-C); 10.7 (s, CH3), 10.1 (s, CH3). HRMS (EI): m/z calculated for C$_{28}$H$_{36}$Co$_2$ (M) 490.1481. found 490.1472.

The structure of the product was characterised by X-Ray crystal diffraction.

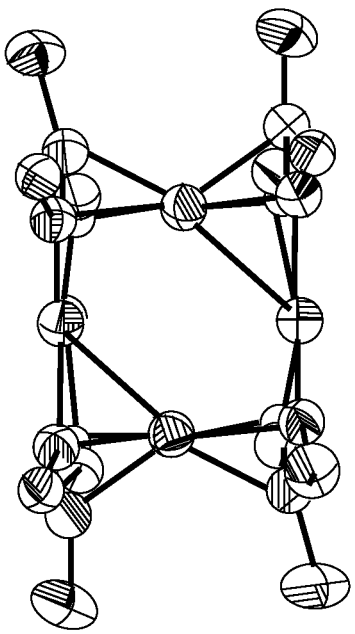

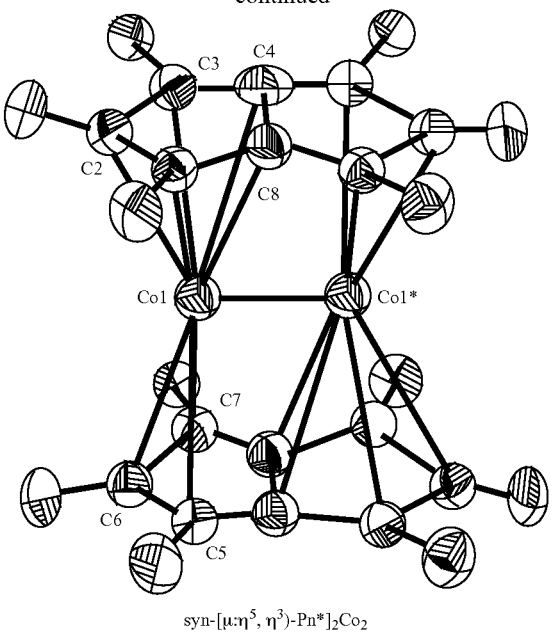

syn-[μ:η$^5$, η$^3$)-Pn*]$_2$Co$_2$

The complex may, for example, be used as an electron transfer material.

Example 17

Synthesis of anti-[(μ:η$^5$, η$^1$)-Pn*][Re(CO)$_3$][Re(CO)$_5$]

Li$_2$Pn*(TMEDA)$_{0.12}$ (1.00 g, 4.67 mmol) and Re(CO)$_5$Br (3.79 g, 9.34 mmol) were combined in Et$_2$O (50 ml) at room temperature and then stirred for 12 hours. Volatiles were removed under reduced pressure and the residue was then extracted with hexane (40 ml) and cooled to −80° C., whereupon white microcrystals were formed.

Yield: 68% (2.49 g). 1H NMR (C6D6, 300 MHz): δ 2.15 (3H, s, CH3), 2.05 (3H, s, CH3), 1.92 (6H, s, CH3), 1.65 (6H, s, CH3). MS (EI): m/z calculated for C$_{22}$H$_{18}$Re$_2$O$_8$ (M) 784.0117. found 784.0101.

The structure of the product was characterised by X-Ray crystal diffraction.

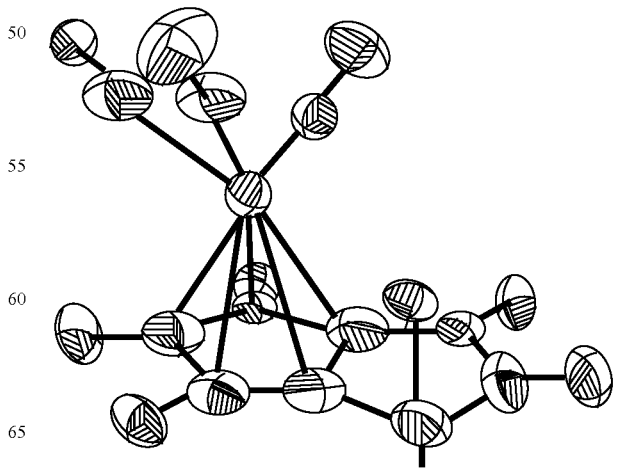

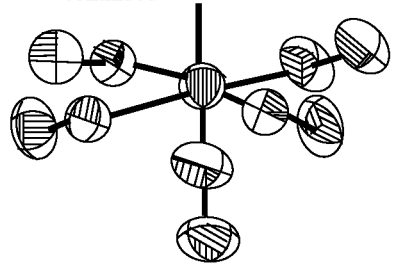

anti-[(μ:η⁵, η¹)-Pn*][Re(CO)₃][Re(CO)₅]

The complex may, for example, be used as a catalyst in C—H bond activation.

Example 18

Synthesis of anti-[(μ:η⁵, η⁵-Pn*][Re(CO)₃]₂

Li₂Pn*(TMEDA)$_{0.12}$ (1.00 g, 4.67 mmol) and [Re(CO)₃(THF)Br]₂ (3.94 g, 4.67 mmol) were combined at −80° C. in THF (50 ml) and then stirred for 12 hours with warming to room temperature. Volatiles were removed under reduced pressure and the residue was then recrystallised from toluene, forming large yellow crystals which were filtered and dried.

Yield: 36% (1.22 g). 1H NMR (C6D6, 300 MHz): δ 1.95 (12H, s, CH3), 1.23 (6H, s, CH3). MS (EI): m/z calculated for C₂₀H₁₈Re₂O₆ (M) 726.0191. found 725.9713.

The structure of the product was characterised by X-Ray crystal diffraction.

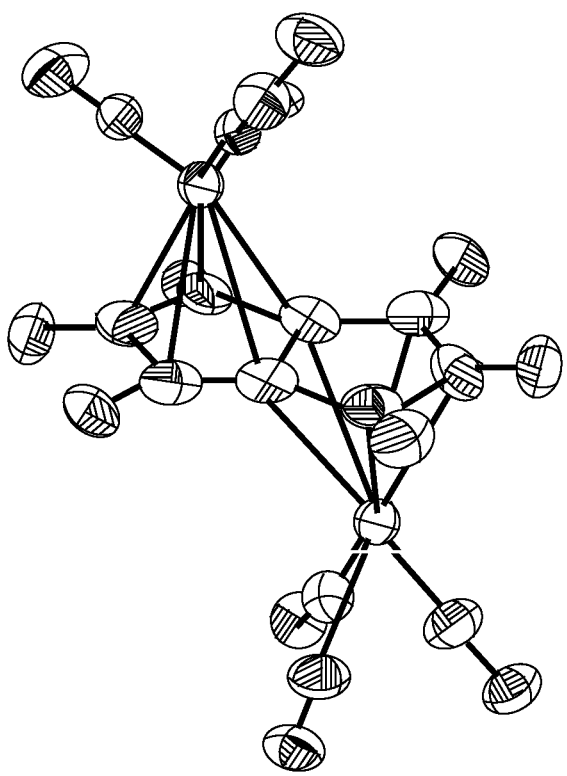

anti-[(μ:η⁵, η⁵)-Pn*][Re(CO)₃]₂

The complex may, for example, be used as a catalyst in C—H bond activation.

The invention claimed is:

1. A compound which is a substituted pentalene of formula (I):

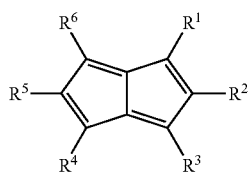

(I)

wherein R¹, R², R³, R⁴, R⁵ and R⁶ are each independently a substituent group having up to 40 carbon atoms, provided that the substituent groups R¹, R², R³, R⁴, R⁵ and R⁶ are not all phenyl.

2. A compound according to claim 1 in which each of the substituent groups R¹, R², R³, R⁴, R⁵ and R⁶ is the same.

3. A compound according to claim 1 in which R² and R⁵ are the same; and/or R¹ and R⁴ are the same; and/or R³ and R⁶ are the same.

4. A compound according to claim 1 in which not all of R¹, R², R³, R⁴, R⁵ and R⁶ are chloride groups.

5. A compound according to claim 1 in which R¹, R², R³, R⁴, R⁵ and R⁶ are such that there are no heteroatoms attached directly to the pentalenic ring.

6. A compound according to claim 1 in which R¹, R², R³, R⁴, R⁵ and R⁶ are each independently a substituent group having up to 20 carbon atoms.

7. A compound according to claim 6 in which R¹, R², R³, R⁴, R⁵ and R⁶ are each independently a substituent group having either no carbon atoms or from 1 to 12 carbon atoms.

8. A compound according to claim 1 in which two or more of R¹, R², R³, R⁴, R⁵ and R⁶ are alkyl, aryl, aralkyl or vinyl groups.

9. A compound according to claim 1 in which R¹, R², R³, R⁴, R⁵ and R⁶ are each independently selected from alkyl, aryl, aralkyl and vinyl groups.

10. A compound according to claim 1 in which R¹, R³, R⁴, and R⁶ are each independently selected from unbranched or branched C1-12 alkyl groups.

11. A compound according to claim 10 in which R¹, R³, R⁴, and R⁶ are each independently selected from unbranched or branched C1-4 alkyl groups.

12. A compound according to claim 1 in which R² and R⁵ are each independently selected from unbranched or branched C1-12 alkyl groups and C6-C12 aryl groups.

13. A compound according to claim 12 in which R² and R⁵ are each independently selected from unbranched or branched C1-4 alkyl groups.

14. A compound which is a substituted pentalene selected from the group consisting of formulae (Ia), (Ib), (Ic), and (Id):

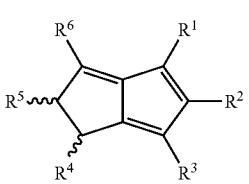

(Ia)

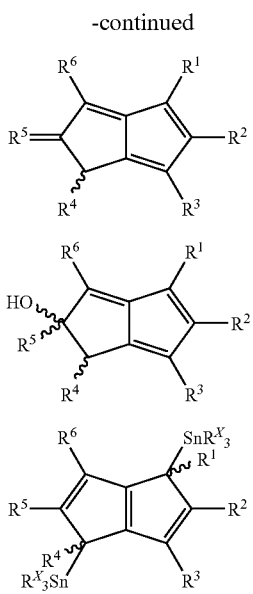

wherein $R^1$, $R^2$, $R^3$, $R^4$, $R^5$ and $R^6$ are each independently a substituent group having up to 40 carbon atoms.

15. A metal complex, which is a complex formed from one or more metal atoms or ions and one or more ligands, wherein one or more of the ligands comprises a compound as defined in any one of claims 1 to 14.

16. A complex according to claim 15 wherein the metal complex is a complex of a single metal atom or ion with one or more ligands.

17. A complex according to claim 15 wherein the metal complex is a complex of two or more metal atoms or ions with one or more ligands.

18. A complex according to claim 15 wherein the metal is a transition metal, lanthanide or actinide atom or ion.

19. A complex according to claim 18 wherein the metal is a Group 3, 4, 5, 6, 7, 8, 9 or 10 transition metal, or a lanthanide metal atom or ion.

20. A method of catalysing a reaction, the method comprising: providing a complex as defined in any one of claims 15 to 19; and using said complex as a catalyst in the reaction.

21. The method according to claim 20, wherein the reaction is an organic transformation.

22. The method according to claim 21, wherein the organic transformation is selected from hydrogenation, hydroformylation, hydrosilylation, hydroamination, C—H activation, C—C bond formation, cyclotrimerisation, oxidation, epoxidation, dihydroxylation, and cycloaddition.

23. The method according to claim 20, wherein the reaction is a polymerisation.

24. The method according to claim 23, wherein the polymerisation is selected from olefinic polymerisation and polymerisation of polar monomers.

25. The method according to claim 23, wherein the polymerisation is selected from oligomerisation, co-polymerisation and homo-polymerisation.

\* \* \* \* \*